(12) United States Patent
Anderson et al.

(10) Patent No.: US 6,548,249 B1
(45) Date of Patent: Apr. 15, 2003

(54) FUSIONS OF SCAFFOLD PROTEINS WITH RANDOM PEPTIDE LIBRARIES

(75) Inventors: David Anderson, San Bruno, CA (US); Beau Robert Peelle, San Francisco, CA (US); Jakob Maria Bogenberger, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/626,581

(22) Filed: Jul. 27, 2000

Related U.S. Application Data

(60) Division of application No. 09/415,765, filed on Oct. 8, 1999, which is a continuation-in-part of application No. 09/169,015, filed on Oct. 8, 1998, now Pat. No. 6,180,343.

(51) Int. Cl.[7] .......................... C12Q 1/68; C12N 15/63; C12N 15/12

(52) U.S. Cl. .................. 435/6; 435/320.1; 536/23.4; 536/23.5

(58) Field of Search ................. 435/6, 320.1; 536/23.4, 536/23.5

(56) References Cited

U.S. PATENT DOCUMENTS

| 5,223,409 | A | * | 6/1993 | Ladner et al. |
| 6,025,485 | A | | 2/2000 | Kamb et al. |
| 6,180,343 | B1 | * | 1/2001 | Anderson et al. |
| 6,232,107 | B1 | * | 5/2001 | Bryan et al. |

FOREIGN PATENT DOCUMENTS

| WO | 95/34664 | | 12/1995 |
| WO | 97/11094 | | 3/1997 |
| WO | 97/45538 | | 12/1997 |
| WO | 98/36097 | | 8/1998 |
| WO | 98/39483 | | 9/1998 |
| WO | 99/24617 | | 5/1999 |
| WO | 99/49019 | | 9/1999 |
| WO | WO99/49019 | * | 9/1999 |

OTHER PUBLICATIONS

McConnell et al., Tendamistat as a Scaffold for Conformationally Constrained Phage Peptide Libraries, J. Mol. Biol (1995), 250, 460–470.*

Chalfie, M. "Green fluorescent protein," Photochemistry and Photobiology, 62(4): 651–656 (1995).

Ward et al., "an Energy Transfer Protein in Coelenterate Bioluminescence," The Journal of Biological Chemistry, 254(3):781–788 (1979).

Yang et al., "The molecular structure of green fluorescent protein," Nature Biotechnology, 14:246–1251 (1996).

Abedi, M.R. et al., "Green Fluorescent Protein as a Scaffold for Intracellular Presentation of Peptides," Nucleic Acids Research, 26(2):623–630 (1988).

Cepko, "Current Protocols in Molecular Biology," vol. 2, ed.Ausubel et al. pp. 9.9.1–9.9.16 (1998).

Longstaff, et al., "Recombinant Chymotrypsin Inhibitor 2: Expression, Kinetic Analysis of Inhibition with alpha–Chymotrypsin and wild–type and Mutant Subtilisin BPN', and Protein Engineering to Investigate Inhibitory Specificity and Mechanism," Biochemistry, 29(31): 7339–73347 (Aug. 7, 1990).

de Prat Gay, et al., "Generation of a Family of Protein Fragments fro Structure–Folding Studies. 1. Folding Complementation of Two Fragments of Chymotrypsin Inhibitor–2 formed by Cleavage at its unique Methionine Residue," Biochemistry, 33(25): 7957–7963 (Jun. 28, 1994).

Jackson, et al., "Folding of Chymotrypsin Inhibitor 2. 1. Evidence for a Two–State Transition," Biochemistry, 30(43): 10428–10435 (Oct. 29, 1991).

McPhalen, et al., "Crystal and Molecular Structure of the Serine Proteinase Inhibitor CI–2 from Barley Seeds," Biochemistry, 26(1): 261–269 (Jan. 13, 1987).

Adachi, et al., "Site–Directed Mutants, at Position 166, of RTEM–1 beta–lactamase that Form a Stable acyl–enzyme Intermediate with Penicillin," J. Biol. Chem., 266(5): 3186–3191 (Feb. 15, 1991).

Bouthors, et al., "Role of Residues 104, 164, 166, 238 and 240 in the Substrate Profile of PER–1 beta–lactamase Hydrolysing Third–Generation Cephalosporins," Biochem J., 330(Pt. 3): 1443–1449 (Mar. 15, 1998).

Huang, et al., "A Natural Polymorphism in beta–lactamase is a Global Suppressor," Proc. Natl. Acad. Sci. USA, 94(16): 8801–8806 (Aug. 5, 1997).

Jelsch, et al., "Crystal Structure of *Escherichia Coli* TEM1 beta–lactamase at 1.8 A Resolution," Proteins, 16(4): 364–383 (Aug. 1993).

Knox, et al., "A Catalytically–Impaired Class A beta–lactamase: 2 A Crystal Structure and Kinetics of the Bacillus Licheniformis E166A Mutant," Protein Eng., 6(1): 11–18 (Jan. 1993).

Legendre, et al., "Engineering a Regulatable Enzyme for Homogeneous Immunoassays," Nat. Biotechnol., 17(1): 67–72 (Jan. 1999).

Marshall, et al., "Evaluation of S1 Chromogenic Cephalosporin Beta–Lactamase Disk Assay Tested Against Gram–Positive Anaerobes, Coagulas–negative Staphylococci, Prevotella spp. and Enterococcus spp.," Diagn. Microbiol. Infect. Dis., 22(4):353–355 (Aug. 1995).

(List continued on next page.)

Primary Examiner—John S. Brusca

(57) ABSTRACT

The invention relates to the use of scaffold proteins, particularly green fluorescent protein (GFP), in fusion constructs with random and defined peptides and peptide libraries, to increase the cellular expression levels, decrease the cellular catabolism, increase the conformational stability relative to linear peptides, and to increase the steady state concentrations of the random peptides and random peptide library members expressed in cells for the purpose of detecting the presence of the peptides and screening random peptide libraries. N-terminal, C-terminal, dual N- and C-terminal and one or more internal fusions are all contemplated. Novel fusions utilizing self-binding peptides to create a conformationally stabilized fusion domain are also contemplated.

33 Claims, 8 Drawing Sheets

OTHER PUBLICATIONS

Raquet, et al., "Stability of TEM Beta–Lactamase Mutants Hydrolyzing Third Generation Cephalosporins," Proteins, 23(1):63–72 (Sep. 1995).

Rodrigues, et al., "Synthesis and Beta–Lactamase–Mediated Activation of a Cephalosporin–Taxol Prodrug," Chem Biol, 2(4):223–227 (Apr. 1995).

Zlokarnik, et al., "Quantitation of Transcription and Clonal Selection of Single Living Cells with Beta–Lactamase as Reporter," Science, 279 (5347):84–88 (Jan. 1998).

Betz, et al., "Controlling Topology and Native–Like Behavior of de Novo–Designed Peptides: Design and Characterization of Antiparallel Four–Stranded Coiled Coils," Biochemistry, 35(21):6955–6962 (May 1996).

Doig, et al., "Structures of N–Termini of Helices in Proteins," Protein Sci, 6(1):147–155 (Jan. 1997).

Doig, et al., "N– and C–Capping Preferences for all 20 Amino Acids in Alpha–Helical Peptides," Protein Sci., 4(7):1325–1336 (Jul. 1995).

Graddis, et al., "Controlled Formation of Model Homo– and Heterodimer Coiled Coil Polypeptides," Biochemistry, 32(47):12664–12671 (Nov. 1993).

Lyu, et al., "Side Chain Contribution to the Stability of Alpha–Helical Structure in Peptides," Science, 250(4981):669–673 (Nov. 1990).

Monera, et al., "Comparison of Antiparallel and Parallel Two–Stranded Alpha–Helical Coiled Coils. Design, Synthesis, and Characerization," J. Biol. Chem., 268(26):19218–19227 (Sep. 15, 1993).

O'Neil, et al., "A Thermodynamic Scale for the Helix–=Forming Tendencies of the Commonly Occurring Amino Acids," Science, 250(4981):646–651 (Nov. 2, 1990).

Richardson, et al., "Amino Acid Preferences for Specific Locations at the Ends of Alpha Helices," Science, 240(4859):1648–1652 (Jun. 17, 1998).

Norman et al., "Genetic Selection of Peptide Inhibitors of Biological Activity," Science, 285(5427):591–595 (Jul. 23, 1999).

Borjigin et al., "Insertional Mutagenesis as a Probe of Rhodopsin's Topography, Stability, and Activity," Journal of Biological Chemistry, 269(20):14715–14722 (1994).

Doi et al., "Screening of conformationally constrained random polypeptide libraries displayed on a protein scaffold," CMLS Cellular and Molecular Life Sciences, 54:394–404 (1998).

Hellinga et al., "Construction of New Ligand Binding Sites in Proteins of Known Structure," J. Mol. Biol. 222:787–803 (1991).

Ladner et al., "Constrained peptides as binding entities," TIBTECH, 13:426–430 (1995).

* cited by examiner

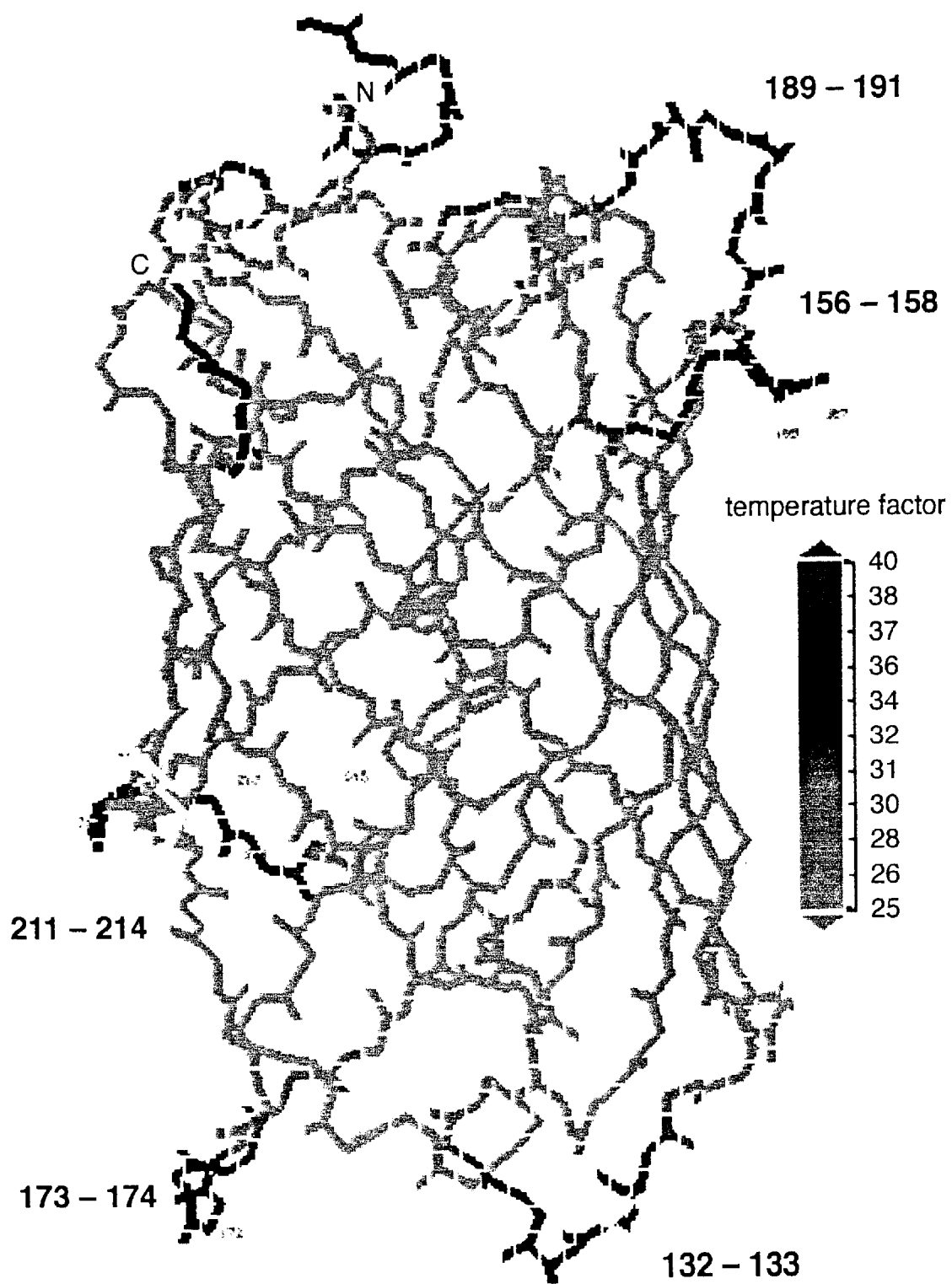
FIG._1

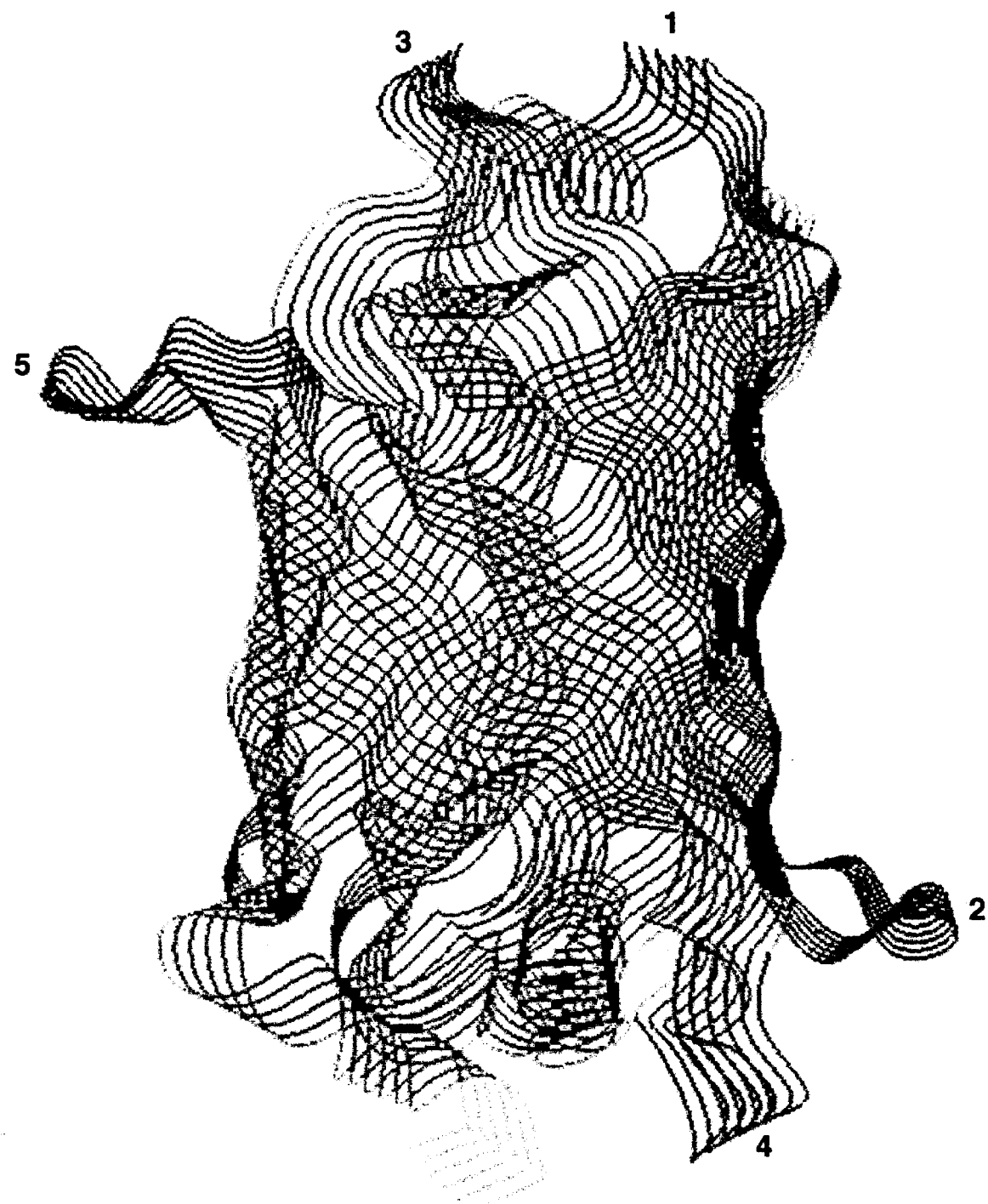
FIG._2A

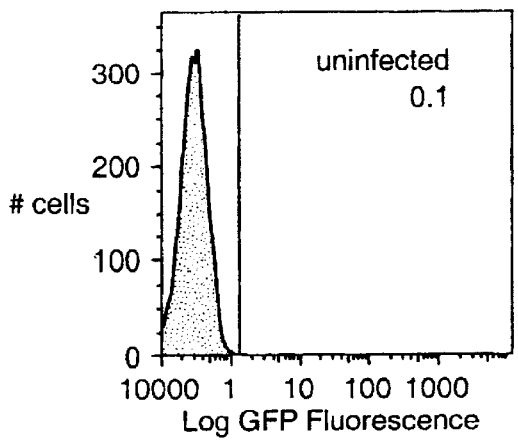
FIG._2B
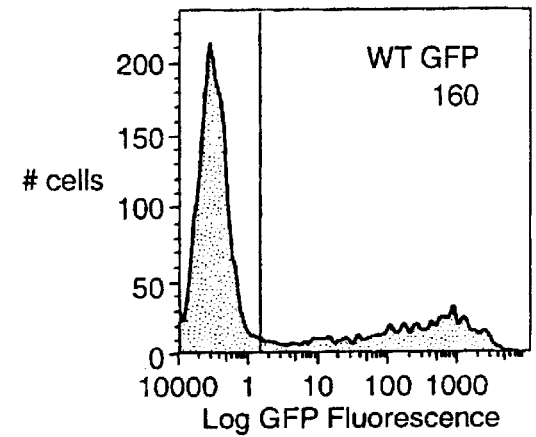
FIG._2C
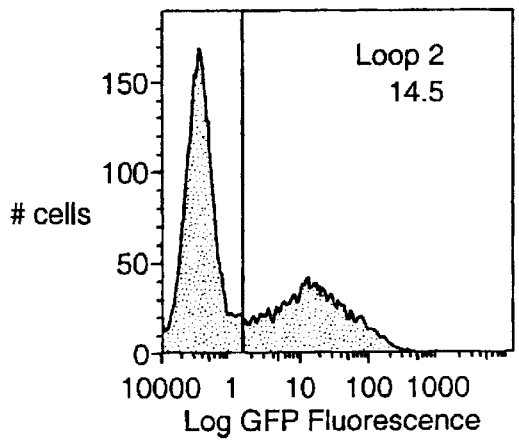
FIG._2D
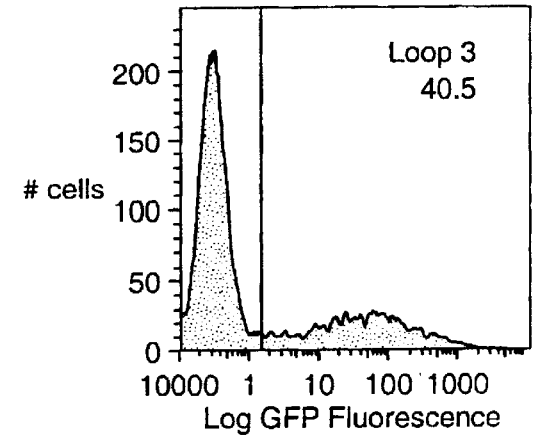
FIG._2E
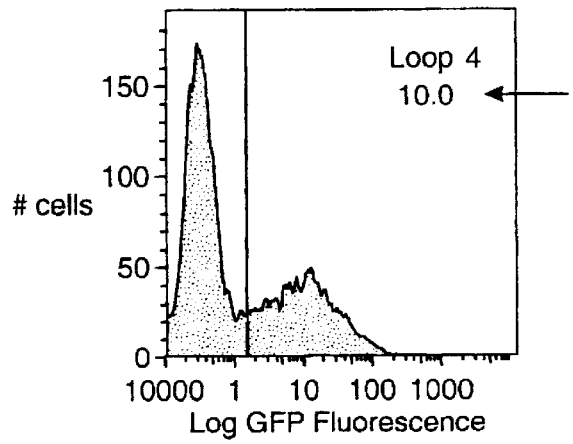
FIG._2F

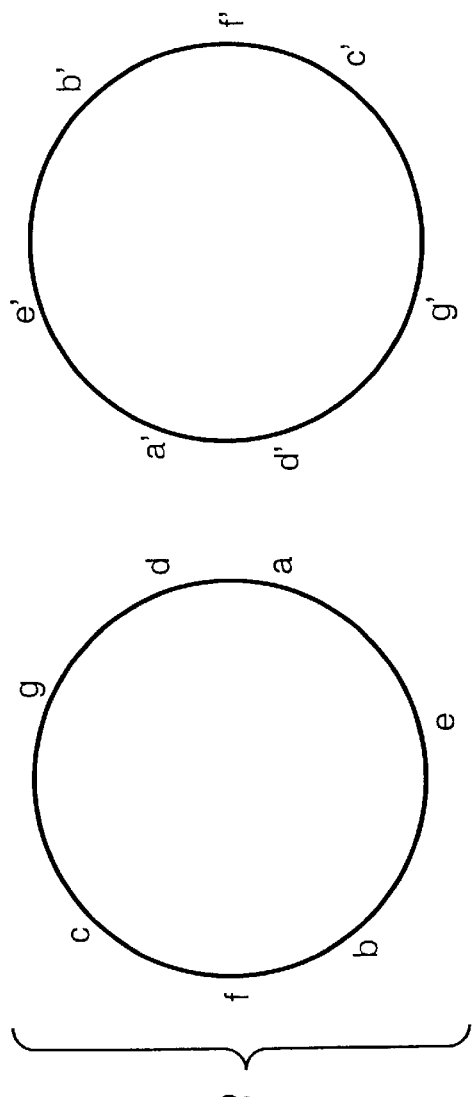

FIG._3

The sequence of beta lactamase TEM-1 from E coli used here includes residues 26-290:

```
HIS 26  PRO GLU THR LEU VAL LYS VAL LYS ASP ALA GLU ASP GLN LEU GLY ALA ARG VAL GLY TYR ILE GLU LEU ASP
LEU ASN SER GLY LYS ILE LEU GLU SER PHE ARG PRO GLU GLU ARG PHE PRO MET MET SER THR PHE LYS VAL LEU LEU
CYS GLY ALA VAL LEU SER ARG ILE ASP ALA GLY GLN GLU GLN LEU GLY ARG ARG ILE HIS TYR SER GLN ASN ASP LEU
VAL GLU TYR SER PRO VAL THR GLU LYS HIS LEU THR ASP GLY MET THR VAL ARG GLU LEU SER ALA ALA ILE THR MET
SER ASP ASN THR ALA ALA ASN LEU LEU LEU THR THR ILE GLY GLY PRO LYS GLU LEU THR ALA PHE LEU HIS ASN MET
GLY ASP HIS VAL THR ARG LEU ASP ARG TRP GLU PRO GLU LEU ASN GLU ALA ILE PRO ASN ASP GLU ARG ASP THR THR
MET PRO VAL ALA MET ALA THR THR LEU ARG LYS LEU LEU THR GLY GLU LEU LEU THR LEU ALA SER ARG GLN GLN LEU
ILE ASP TRP MET GLU ALA ASP LYS VAL ALA GLY PRO LEU LEU ARG SER ALA LEU PRO ALA GLY TRP PHE ILE ALA ASP
LYS SER GLY ALA GLY GLU ARG GLY SER ARG GLY ILE ILE ALA ALA LEU GLY PRO ASP GLY LYS PRO SER ARG ILE VAL
VAL ILE TYR THR THR GLY SER GLN ALA THR MET ASP GLU ARG ASN ARG GLN ILE ALA GLU ILE GLY ALA SER LEU ILE
LYS HIS TRP 290
```

FIG._4

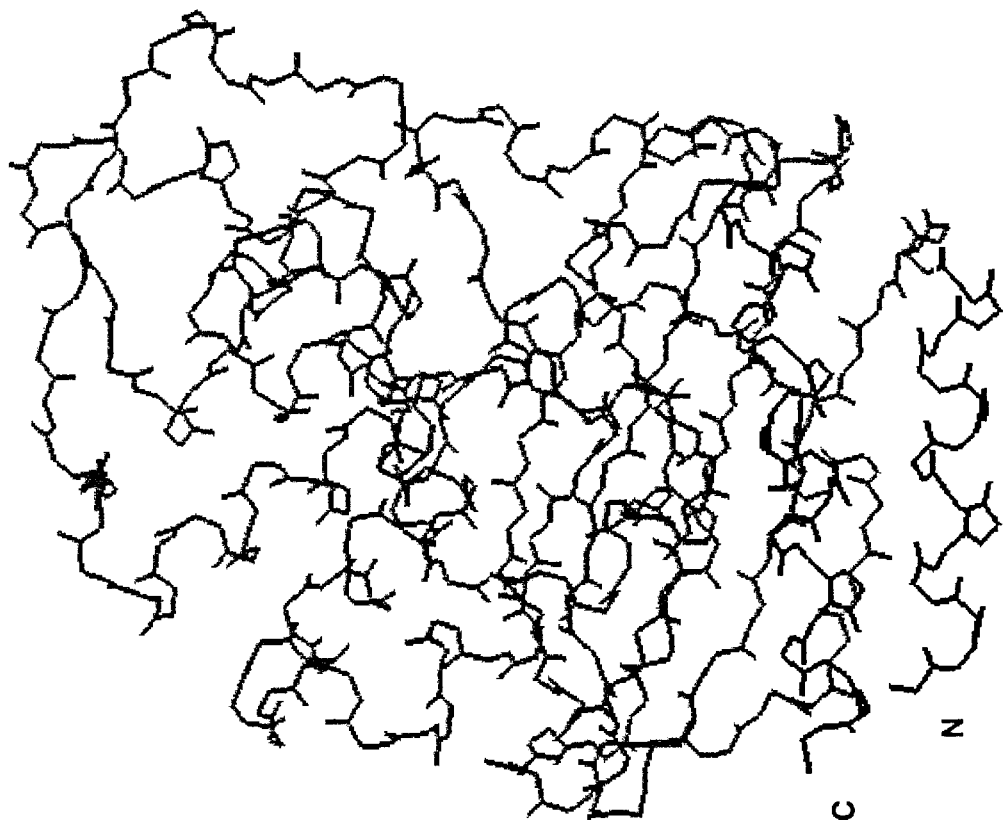
FIG._5B
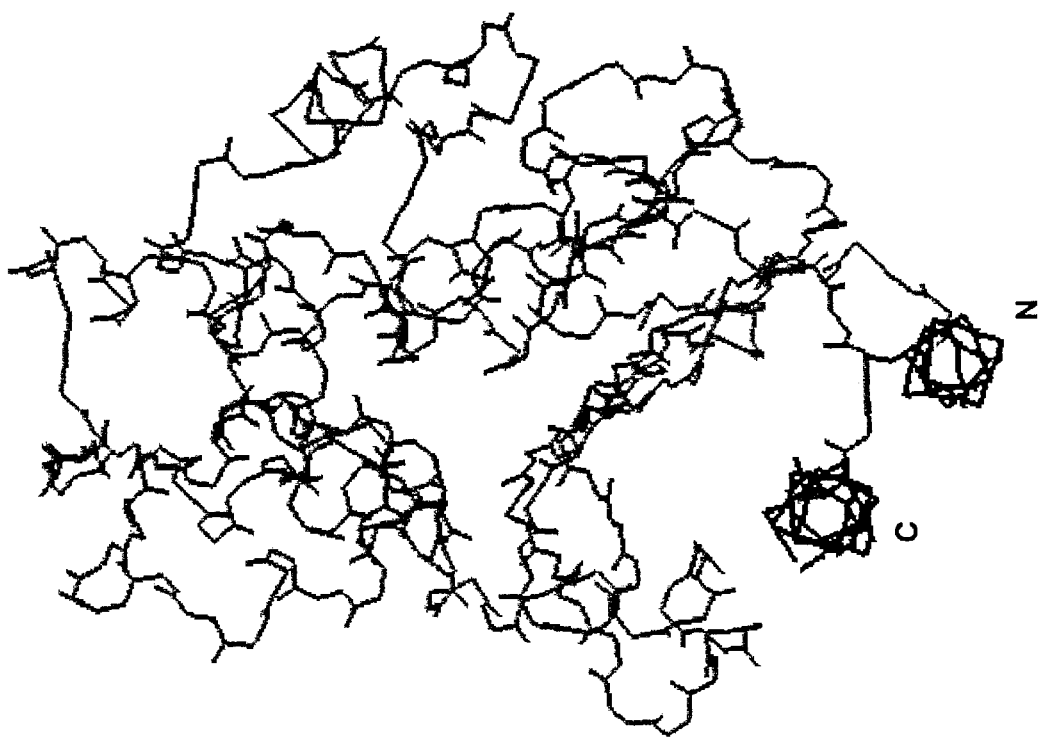
FIG._5A

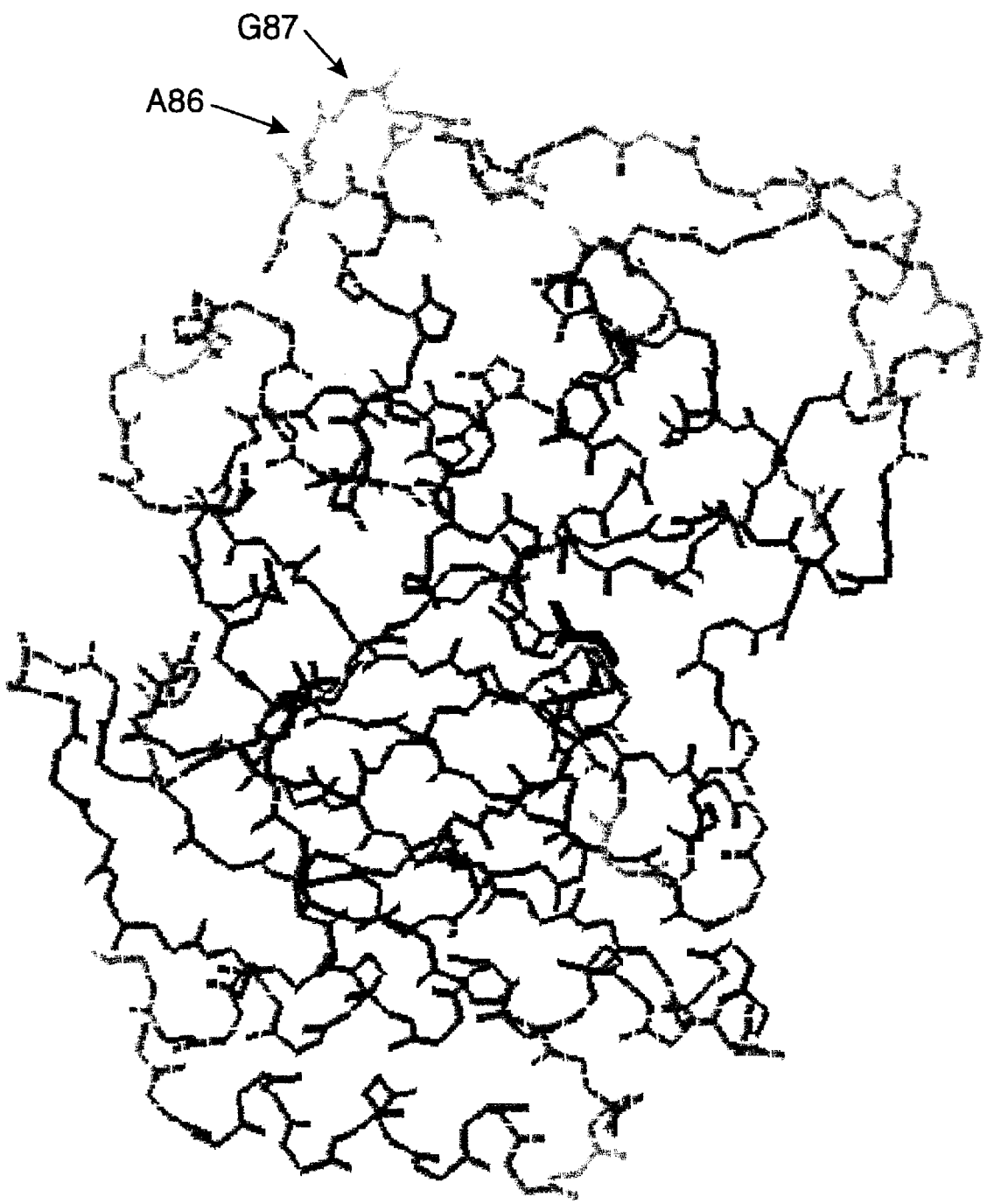
FIG._6

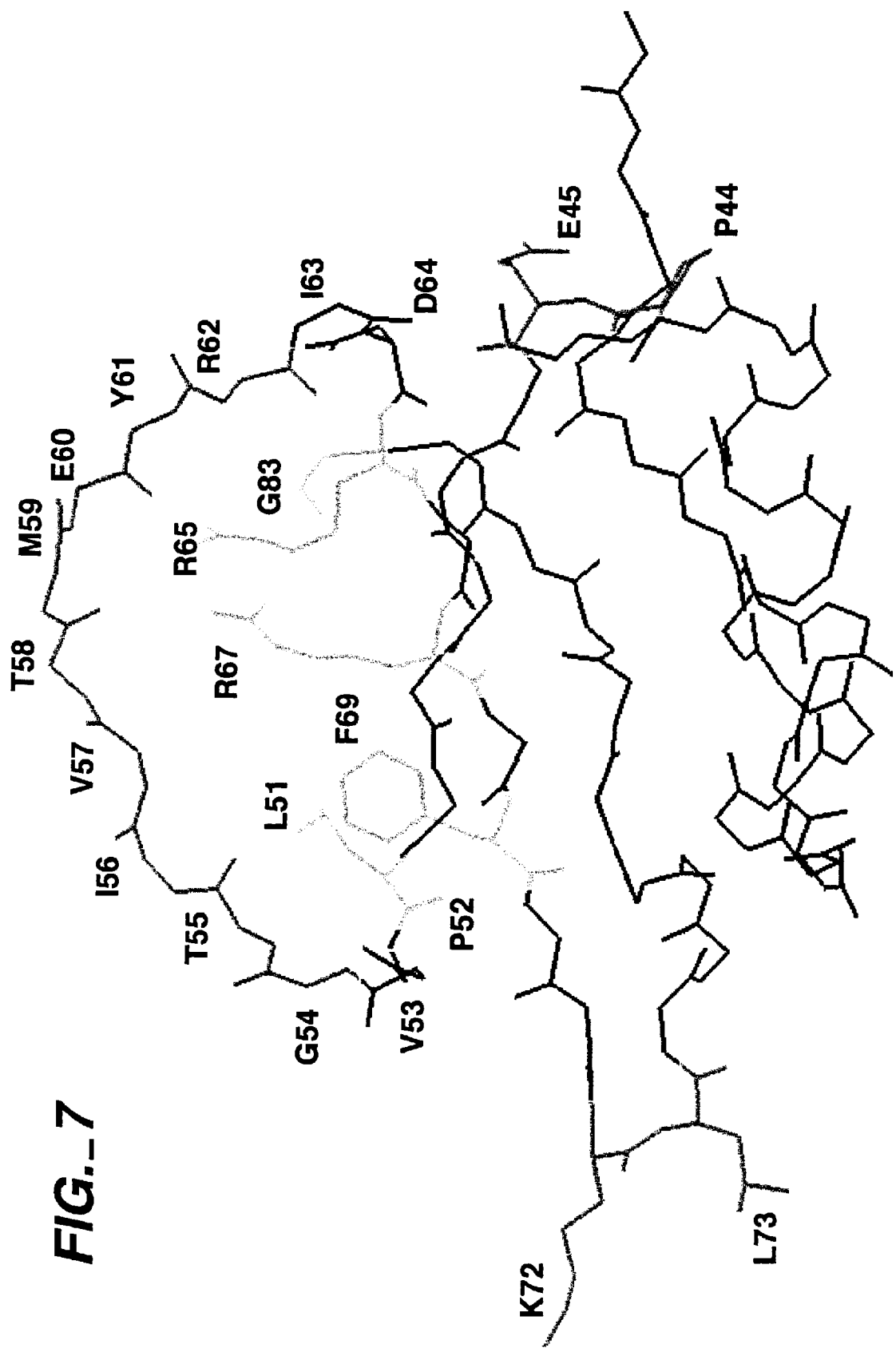
FIG._7

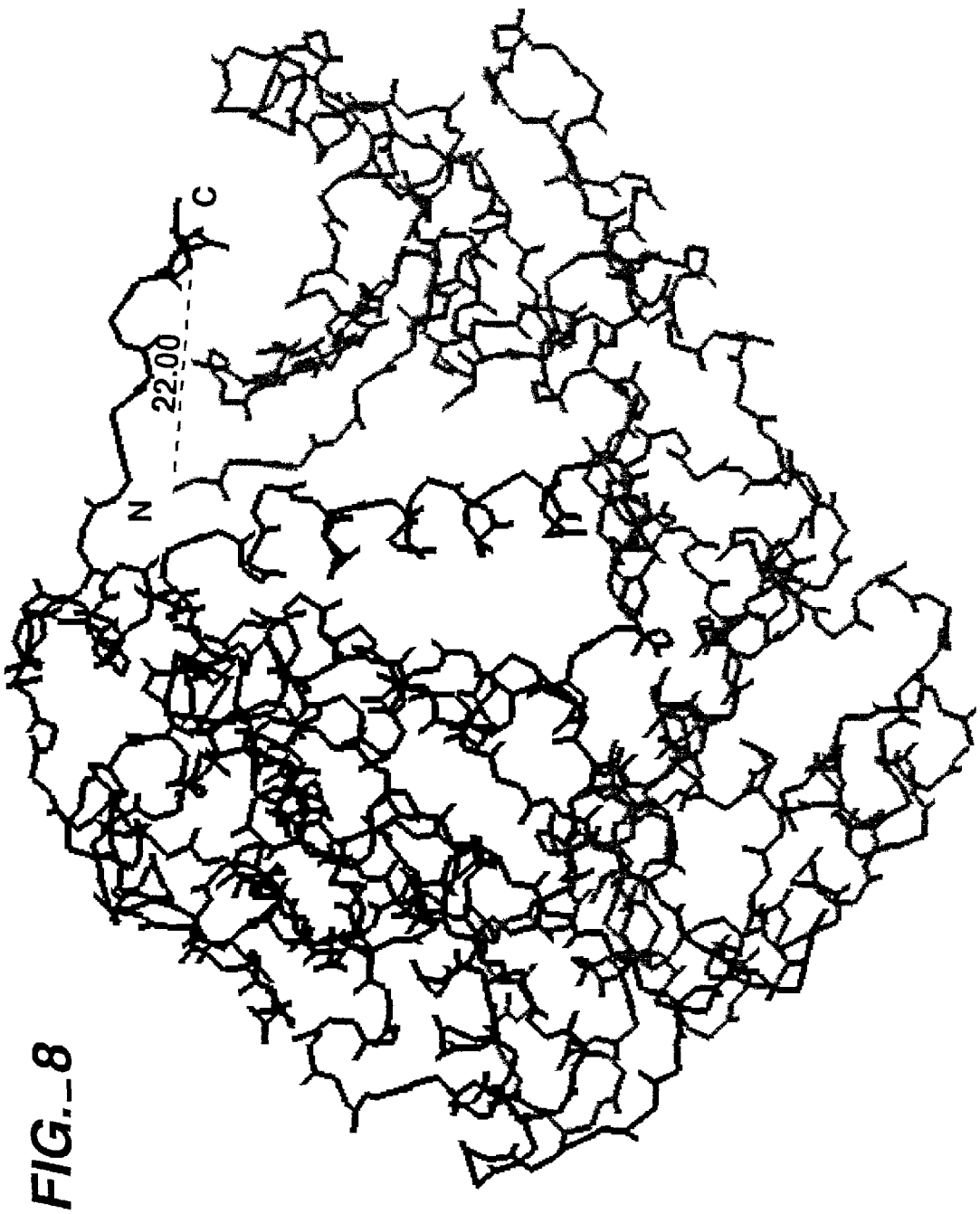
FIG._8

SEQUENCE LISTING

```
<160> NUMBER OF SEQ ID NOS: 65

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  synthetic

<400> SEQUENCE: 1

Leu Glu Glu Phe Gly Ser
  1               5

<210> SEQ ID NO 2
<211> LENGTH: 11
<212> TYPE: PRT
<213> ORGANISM: Artificial Sequence
```

-continued

```
<220> FEATURE:
<223> OTHER INFORMATION: Description of Artificial Sequence:  synthetic

<400> SEQUENCE: 2

Tyr Pro Tyr Asp Val Pro Asp Tyr Ala Ser Leu
 1               5                  10

<210> SEQ ID NO 3
<211> LENGTH: 262
<212> TYPE: PRT
<213> ORGANISM: E. coli

<400> SEQUENCE: 3

His Pro Glu Thr Leu Val Lys Val Lys Asp Ala Glu Asp Gln Leu Gly
 1               5                  10                  15

Ala Arg Val Gly Tyr Ile Glu Leu Asp Leu Asn Ser Gly Lys Ile Leu
                20                  25                  30

Glu Ser Phe Arg Pro Glu Arg Phe Pro Met Met Ser Thr Phe Lys
            35                  40                  45

Val Leu Leu Cys Gly Ala Val Leu Ser Arg Ile Asp Ala Gly Gln Glu
        50                  55                  60

Gln Leu Gly Arg Arg Ile His Tyr Ser Gln Asn Asp Leu Val Glu Tyr
 65                  70                  75                  80

Ser Pro Val Thr Glu Lys His Leu Thr Asp Gly Met Thr Val Arg Glu
                85                  90                  95

Leu Ser Ala Ala Ile Thr Met Ser Asp Asn Thr Ala Ala Asn Leu Leu
               100                 105                 110

Leu Thr Thr Ile Gly Gly Pro Lys Glu Leu Thr Ala Phe Leu His Asn
            115                 120                 125

Met Gly Asp His Val Thr Arg Leu Asp Arg Trp Glu Pro Glu Leu Asn
        130                 135                 140

Glu Ala Ile Pro Asn Asp Glu Arg Asp Thr Thr Met Pro Val Ala Met
145                 150                 155                 160

Ala Thr Thr Leu Arg Lys Leu Leu Thr Gly Glu Leu Leu Thr Leu Ala
                165                 170                 175

Ser Arg Gln Gln Leu Ile Asp Trp Met Glu Ala Asp Lys Val Ala Gly
            180                 185                 190

Pro Leu Leu Arg Ser Ala Leu Pro Ala Gly Trp Phe Ile Ala Asp Lys
        195                 200                 205

Ser Gly Ala Gly Glu Arg Gly Ser Arg Gly Ile Ile Ala Ala Leu Gly
    210                 215                 220

Pro Asp Gly Lys Pro Ser Arg Ile Val Val Ile Tyr Thr Thr Gly Ser
225                 230                 235                 240

Gln Ala Thr Met Asp Glu Arg Asn Arg Gln Ile Ala Glu Ile Gly Ala
                245                 250                 255

Ser Leu Ile Lys His Trp
            260

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 4

Lys Leu Glu Ala Leu Glu Gly
 1               5
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 5

Glu Glu Ala Ala Lys Ala
 1               5

<210> SEQ ID NO 6
<211> LENGTH: 9
<212> TYPE: PRT
<213> ORGANISM: Artificial Sequence
<220> FEATURE:
<221> NAME/KEY: UNSURE
<222> LOCATION: (1)..(3)
<223> OTHER INFORMATION: The x at positions 1, 2 and 3 represents a
      randomized residue.
<220> FEATURE:
<221> NAME/KEY: UNSURE
<222> LOCATION: (6)
<223> OTHER INFORMATION: The x at position 6 represents a randomized
      residue.
<220> FEATURE:
<221> NAME/KEY: UNSURE
<222> LOCATION: (8)..(9)
<223> OTHER INFORMATION: The x at positions 8 and 9 represents a
      randomized residue.
<220> FEATURE:
<223> OTHER INFORMATION: Description of Artificial Sequence: synthetic

<400> SEQUENCE: 6

Xaa Xaa Xaa Pro Pro Xaa Pro Xaa Xaa
 1               5

<210> SEQ ID NO 7
<211> LENGTH: 61
<212> TYPE: PRT
<213> ORGANISM: Artificial Sequence
<220> FEATURE:
<223> OTHER INFORMATION: Description of Artificial Sequence: synthetic

<400> SEQUENCE: 7

Met Gly Cys Ala Ala Leu Glu Ser Glu Val Ser Ala Leu Glu Ser Glu
 1               5                  10                  15

Val Ala Ser Leu Glu Ser Glu Val Ala Ala Leu Gly Arg Gly Asp Met
             20                  25                  30

Pro Leu Ala Ala Val Lys Ser Lys Leu Ser Ala Val Lys Ser Lys Leu
         35                  40                  45

Ala Ser Val Lys Ser Lys Leu Ala Ala Cys Gly Pro Pro
     50                  55                  60

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 8

Gly Arg Gly Asp Met Pro
 1               5

<210> SEQ ID NO 9

```
<211> LENGTH: 69
<212> TYPE: PRT
<213> ORGANISM: Artificial Sequence
<220> FEATURE:
<223> OTHER INFORMATION: Description of Artificial Sequence:  synthetic

<400> SEQUENCE: 9

Met Gly Arg Asn Ser Gln Ala Thr Ser Gly Phe Thr Phe Ser His Phe
 1               5                  10                  15

Tyr Met Glu Trp Val Arg Gly Gly Glu Tyr Ile Ala Ala Ser Arg His
             20                  25                  30

Lys His Asn Lys Tyr Thr Thr Glu Tyr Ser Ala Ser Val Lys Gly Arg
         35                  40                  45

Tyr Ile Val Ser Arg Asp Thr Ser Gln Ser Ile Leu Tyr Leu Gln Lys
     50                  55                  60

Lys Lys Gly Pro Pro
 65

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:  synthetic

<400> SEQUENCE: 10

Phe Gln Cys Glu Glu Cys
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 11

His Ile Arg Ser His Thr Gly
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:  synthetic

<400> SEQUENCE: 12

Val Lys Cys Phe Asn Cys
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 13

His Thr Ala Arg Asn Cys Arg
 1               5

<210> SEQ ID NO 14
<211> LENGTH: 9
<212> TYPE: PRT
```

```
<213> ORGANISM: Artificial Sequence
<220> FEATURE:
<223> OTHER INFORMATION: Description of Artificial Sequence:  synthetic

<400> SEQUENCE: 14

Met Asn Pro Asn Cys Ala Arg Cys Gly
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:  synthetic

<400> SEQUENCE: 15

His Lys Ala Cys Phe
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 16

Glu Phe Leu Ile Val Lys Ser
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:  synthetic

<400> SEQUENCE: 17

Glu Glu Phe Leu Ile Val Lys Lys Ser
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 18

Phe Glu Ser Ile Lys Leu Val
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 19

Val Ser Ile Lys Phe Glu Leu
 1               5

<210> SEQ ID NO 20
<211> LENGTH: 7
<212> TYPE: PRT
<213> ORGANISM: Monkey virus
```

```
<400> SEQUENCE: 20

Pro Lys Lys Lys Arg Lys Val
  1               5

<210> SEQ ID NO 21
<211> LENGTH: 6
<212> TYPE: PRT
<213> ORGANISM: Homo sapiens

<400> SEQUENCE: 21

Ala Arg Arg Arg Arg Pro
  1               5

<210> SEQ ID NO 22
<211> LENGTH: 10
<212> TYPE: PRT
<213> ORGANISM: Homo sapiens

<400> SEQUENCE: 22

Glu Glu Val Gln Arg Lys Arg Gln Lys Leu
  1               5                  10

<210> SEQ ID NO 23
<211> LENGTH: 9
<212> TYPE: PRT
<213> ORGANISM: Homo sapiens

<400> SEQUENCE: 23

Glu Glu Lys Arg Lys Arg Thr Tyr Glu
  1               5

<210> SEQ ID NO 24
<211> LENGTH: 20
<212> TYPE: PRT
<213> ORGANISM: Xenopus

<400> SEQUENCE: 24

Ala Val Lys Arg Pro Ala Ala Thr Lys Lys Ala Gly Gln Ala Lys Lys
  1               5                  10                  15

Lys Lys Leu Asp
             20

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: synthetic

<400> SEQUENCE: 25

Met Ala Ser Pro Leu Thr Arg Phe Leu Ser Leu Asn Leu Leu Leu Leu
  1               5                  10                  15

Gly Glu Ser Ile Leu Gly Ser Gly Glu Ala Lys Pro Gln Ala Pro
             20                  25                  30

<210> SEQ ID NO 26
<211> LENGTH: 21
<212> TYPE: PRT
<213> ORGANISM: Homo sapiens

<400> SEQUENCE: 26

Met Ser Ser Phe Gly Tyr Arg Thr Leu Thr Val Ala Leu Phe Thr Leu
  1               5                  10                  15
```

```
Ile Cys Cys Pro Gly
            20

<210> SEQ ID NO 27
<211> LENGTH: 51
<212> TYPE: PRT
<213> ORGANISM: Mouse

<400> SEQUENCE: 27

Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
        35                  40                  45

His Ser Arg
        50

<210> SEQ ID NO 28
<211> LENGTH: 33
<212> TYPE: PRT
<213> ORGANISM: Homo sapiens

<400> SEQUENCE: 28

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: synthetic

<400> SEQUENCE: 29

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Val Thr Met
            20                  25                  30

Gly Leu Leu Thr
        35

<210> SEQ ID NO 30
<211> LENGTH: 14
<212> TYPE: PRT
<213> ORGANISM: Chicken

<400> SEQUENCE: 30

Met Gly Ser Ser Lys Ser Lys Pro Lys Asp Pro Ser Gln Arg
1               5                   10

<210> SEQ ID NO 31
<211> LENGTH: 26
<212> TYPE: PRT
<213> ORGANISM: Artificial Sequence
<220> FEATURE:
<223> OTHER INFORMATION: Description of Artificial Sequence: synthetic

<400> SEQUENCE: 31
```

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: synthetic

<400> SEQUENCE: 32

Lys Gln Phe Arg Asn Cys Met Thr Ser Leu Cys Cys Gly Lys Asn Pro
1               5                   10                  15

Leu Gly Asp

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: synthetic

<400> SEQUENCE: 33

Leu Asn Pro Pro Asp Glu Ser Gly Pro Gly Cys Met Ser Cys Lys Cys
1               5                   10                  15

Val Leu Ser

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 34

Lys Phe Glu Arg Gln
1               5

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: synthetic

<400> SEQUENCE: 35

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35

<210> SEQ ID NO 36
<211> LENGTH: 35
<212> TYPE: PRT
<213> ORGANISM: Homo sapiens

<400> SEQUENCE: 36

Leu Val Pro Ile Ala Val Gly Ala Ala Leu Ala Gly Val Leu Ile Leu
1               5                   10                  15

```
Val Leu Leu Ala Tyr Phe Ile Gly Leu Lys His His His Ala Gly Tyr
            20                  25                  30

Glu Gln Phe
        35
```

<210> SEQ ID NO 37
<211> LENGTH: 27
<212> TYPE: PRT
<213> ORGANISM: Yeast

<400> SEQUENCE: 37

```
Met Leu Arg Thr Ser Ser Leu Phe Thr Arg Arg Val Gln Pro Ser Leu
  1               5                  10                  15

Phe Ser Arg Asn Ile Leu Arg Leu Gln Ser Thr
            20                  25
```

<210> SEQ ID NO 38
<211> LENGTH: 25
<212> TYPE: PRT
<213> ORGANISM: Yeast

<400> SEQUENCE: 38

```
Met Leu Ser Leu Arg Gln Ser Ile Arg Phe Phe Lys Pro Ala Thr Arg
  1               5                  10                  15

Thr Leu Cys Ser Ser Arg Tyr Leu Leu
            20                  25
```

<210> SEQ ID NO 39
<211> LENGTH: 64
<212> TYPE: PRT
<213> ORGANISM: Yeast

<400> SEQUENCE: 39

```
Met Phe Ser Met Leu Ser Lys Arg Trp Ala Gln Arg Thr Leu Ser Lys
  1               5                  10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
     50                  55                  60
```

<210> SEQ ID NO 40
<211> LENGTH: 41
<212> TYPE: PRT
<213> ORGANISM: Yeast

<400> SEQUENCE: 40

```
Met Lys Ser Phe Ile Thr Arg Asn Lys Thr Ala Ile Leu Ala Thr Val
  1               5                  10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40
```

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: synthetic

```
<400> SEQUENCE: 41

Lys Asp Glu Leu
  1

<210> SEQ ID NO 42
<211> LENGTH: 15
<212> TYPE: PRT
<213> ORGANISM: Adenovirus

<400> SEQUENCE: 42

Leu Tyr Leu Ser Arg Arg Ser Phe Ile Asp Glu Lys Lys Met Pro
  1               5                  10                  15

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence:  synthetic

<400> SEQUENCE: 43

Leu Asn Pro Pro Asp Glu Ser Gly Pro Gly Cys Met Ser Cys Lys Cys
  1               5                  10                  15

Val Leu Ser

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence:  synthetic

<400> SEQUENCE: 44

Leu Thr Glu Pro Thr Gln Pro Thr Arg Asn Gln Cys Cys Ser Asn
  1               5                  10                  15

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence:  synthetic

<400> SEQUENCE: 45

Arg Thr Ala Leu Gly Asp Ile Gly Asn
  1               5

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence:  synthetic

<400> SEQUENCE: 46

Met Tyr Arg Met Gln Leu Leu Ser Cys Ile Ala Leu Ser Leu Ala Ala
  1               5                  10                  15

Leu Val Thr Asn Ser
             20

<210> SEQ ID NO 47
<211> LENGTH: 29
<212> TYPE: PRT
<213> ORGANISM: Artificial Sequence
```

```
<220> FEATURE:
<223> OTHER INFORMATION: Description of Artificial Sequence:  synthetic

<400> SEQUENCE: 47

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr
             20                  25

<210> SEQ ID NO 48
<211> LENGTH: 27
<212> TYPE: PRT
<213> ORGANISM: Preproinsulin

<400> SEQUENCE: 48

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn
             20                  25

<210> SEQ ID NO 49
<211> LENGTH: 18
<212> TYPE: PRT
<213> ORGANISM: Influenza virus

<400> SEQUENCE: 49

Met Lys Ala Lys Leu Leu Val Leu Leu Tyr Ala Phe Val Ala Gly Asp
  1               5                  10                  15

Gln Ile

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence:  synthetic

<400> SEQUENCE: 50

Met Gly Leu Thr Ser Gln Leu Leu Pro Pro Leu Phe Phe Leu Leu Ala
  1               5                  10                  15

Cys Ala Gly Asn Phe Val His Gly
             20

<210> SEQ ID NO 51
<211> LENGTH: 10
<212> TYPE: PRT
<213> ORGANISM: Artificial Sequence
<220> FEATURE:
<221> NAME/KEY: UNSURE
<222> LOCATION: (3)..(6)
<223> OTHER INFORMATION: The x at positions 3, 4, 5 and 6 represents any
      amino acid.
<220> FEATURE:
<223> OTHER INFORMATION: Description of Artificial Sequence:  synthetic

<400> SEQUENCE: 51

Met Gly Xaa Xaa Xaa Xaa Gly Gly Pro Pro
  1               5                  10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:  synthetic
```

```
<400> SEQUENCE: 52

Gly Ser Gly Gly Ser
  1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 53

Gly Gly Gly Ser
  1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 54

Gly Gln Gly Gly Gly
  1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 55

Gly Gln Ala Gly Gly Gly Gly
  1               5

<210> SEQ ID NO 56
<211> LENGTH: 12
<212> TYPE: PRT
<213> ORGANISM: Artificial Sequence
<220> FEATURE:
<221> NAME/KEY: UNSURE
<222> LOCATION: (2)..(11)
<223> OTHER INFORMATION: The x at positions 2, 3, 4, 5, 6, 7, 8, 9, 10
      and 11 represents randome cyclized peptide.
<220> FEATURE:
<223> OTHER INFORMATION: Description of Artificial Sequence: synthetic

<400> SEQUENCE: 56

Cys Xaa Xaa Xaa Xaa Xaa Xaa Xaa Xaa Xaa Xaa Cys
  1               5                  10

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: synthetic

<400> SEQUENCE: 57

Gly Gly Gly Gly Tyr Pro Tyr Asp Val Pro Asp Tyr Ala Ser Leu Gly
  1               5                  10                  15

Gly Gly Gly
```

```
<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence:  synthetic

<400> SEQUENCE: 58

Gly Gly Gly Gly Tyr Pro Tyr Asp Gly Gly Gly Gly
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:  synthetic

<400> SEQUENCE: 59

Lys His Trp Glu Glu Ala Ala Lys Ala
 1               5

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence:  synthetic

<400> SEQUENCE: 60

Ala Ala Lys Ala
 1

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence:  synthetic

<400> SEQUENCE: 61

Ala Glu Lys Ala Lys Ala Glu
 1               5

<210> SEQ ID NO 62
<211> LENGTH: 60
<212> TYPE: DNA
<213> ORGANISM: Artificial sequence
<220> FEATURE:
<223> OTHER INFORMATION: Description of Artificial Sequence:  synthetic
<220> FEATURE:
<221> NAME/KEY: CDS
<222> LOCATION: (1)..(60)
<223> OTHER INFORMATION:
<220> FEATURE:
<221> NAME/KEY: misc_feature
<222> LOCATION: (7)..(20)
<223> OTHER INFORMATION: "n" at positions 7-8, 10-11, 13-14, 16-17,
      and 19-20 can be any base.

<400> SEQUENCE: 62 atg ggc nnk nnk nnk nnk nnk aga cct ctg cct cca sbk cct sbk sbk        48
Met Gly Xaa Xaa Xaa Xaa Xaa Arg Pro Leu Pro Pro Xaa Pro Xaa Xaa
 1               5                  10                  15 gga ggc cca cct                                                         60
Gly Gly Pro Pro
            20
```

```
<210> SEQ ID NO 63
<211> LENGTH: 20
<212> TYPE: PRT
<213> ORGANISM: Artificial sequence
<220> FEATURE:
<223> OTHER INFORMATION: Description of Artificial Sequence:  synthetic
<220> FEATURE:
<221> NAME/KEY: misc_feature
<222> LOCATION: (3)..(7)
<223> OTHER INFORMATION: The 'Xaa' at locations 3-7 can be any amino
      acid.
<220> FEATURE:
<221> NAME/KEY: misc_feature
<222> LOCATION: (13)..(13)
<223> OTHER INFORMATION: The 'Xaa' at location 13 indicates a bias
      towards a hydrophobic residue, i.e. Gly, Ala, Val, Arg, Pro, or
      Leu.
<220> FEATURE:
<221> NAME/KEY: misc_feature
<222> LOCATION: (15)..(16)
<223> OTHER INFORMATION: The 'Xaa' at locations 15-16 indicates a bias
      towards a hydrophobic residue, i.e. Gly, Ala, Val, Arg, Pro, or
      Leu.

<400> SEQUENCE: 63

Met Gly Xaa Xaa Xaa Xaa Xaa Arg Pro Leu Pro Pro Xaa Pro Xaa Xaa
1               5                   10                  15

Gly Gly Pro Pro
            20

<210> SEQ ID NO 64
<211> LENGTH: 1079
<212> TYPE: DNA
<213> ORGANISM: Renilla muelleri
<220> FEATURE:
<221> NAME/KEY: CDS
<222> LOCATION: (259)..(975)
<223> OTHER INFORMATION:

<400> SEQUENCE: 64
ggttatacac aagtgtatcg cgtatctgca gacgcatcta gtgggattat tcgagcggta      60
gtatttacgt cagacctgtc taatcgaaac cacaacaaac tcttaaaata agccacattt     120
acataatatc taagagacgc ctcatttaag agtagtaaaa atataatata tgatagagta     180
tacaactctc gccttagaca gacagtgtgc aacagagtaa ctcttgttaa tgcaatcgaa     240
agcgtcaaga gagataag atg agt aaa caa ata ttg aag aac act tgt tta       291
                    Met Ser Lys Gln Ile Leu Lys Asn Thr Cys Leu
                    1               5                   10 caa gaa gta atg tcg tat aaa gta aat ctg gaa gga att gta aac aac       339
Gln Glu Val Met Ser Tyr Lys Val Asn Leu Glu Gly Ile Val Asn Asn
            15                  20                  25 cat gtt ttt aca atg gag ggt tgc ggc aaa ggg aat att tta ttc ggc       387
His Val Phe Thr Met Glu Gly Cys Gly Lys Gly Asn Ile Leu Phe Gly
        30                  35                  40 aat caa ctg gtt cag att cgt gtc acg aaa ggg gcc cca ctg cct ttt       435
Asn Gln Leu Val Gln Ile Arg Val Thr Lys Gly Ala Pro Leu Pro Phe
    45                  50                  55 gca ttt gat att gtg tca cca gct ttt caa tat ggc aac cgt act ttc       483
Ala Phe Asp Ile Val Ser Pro Ala Phe Gln Tyr Gly Asn Arg Thr Phe
60                  65                  70                  75 acg aaa tat ccg aat gat ata tca gat tat ttt ata caa tca ttt cca       531
Thr Lys Tyr Pro Asn Asp Ile Ser Asp Tyr Phe Ile Gln Ser Phe Pro
                80                  85                  90 gca gga ttt atg tat gaa cga aca tta cgt tac gaa gat ggc gga ctt       579
Ala Gly Phe Met Tyr Glu Arg Thr Leu Arg Tyr Glu Asp Gly Gly Leu
            95                  100                 105
```

```
gtt gaa att cgt tca gat ata aat tta ata gaa gac aag ttc gtc tac      627
Val Glu Ile Arg Ser Asp Ile Asn Leu Ile Glu Asp Lys Phe Val Tyr
        110                 115                 120 aga gtg gaa tac aaa ggt agt aac ttc cca gat gat ggt ccc gtc atg      675
Arg Val Glu Tyr Lys Gly Ser Asn Phe Pro Asp Asp Gly Pro Val Met
125                 130                 135 cag aag act atc tta gga ata gag cct tca ttt gaa gcc atg tac atg      723
Gln Lys Thr Ile Leu Gly Ile Glu Pro Ser Phe Glu Ala Met Tyr Met
140                 145                 150                 155 aat aat ggc gtc ttg gtc ggc gaa gta att ctt gtc tat aaa cta aac      771
Asn Asn Gly Val Leu Val Gly Glu Val Ile Leu Val Tyr Lys Leu Asn
                160                 165                 170 tct ggg aaa tat tat tca tgt cac atg aaa aca tta atg aag tcg aaa      819
Ser Gly Lys Tyr Tyr Ser Cys His Met Lys Thr Leu Met Lys Ser Lys
                175                 180                 185 ggt gta gta aag gag ttt cct tcg tat cat ttt att caa cat cgt ttg      867
Gly Val Val Lys Glu Phe Pro Ser Tyr His Phe Ile Gln His Arg Leu
                190                 195                 200 gaa aag act tac gta gaa gac ggg ggg ttc gtt gaa cag cat gag act      915
Glu Lys Thr Tyr Val Glu Asp Gly Gly Phe Val Glu Gln His Glu Thr
        205                 210                 215 gct att gct caa atg aca tct ata gga aaa cca cta gga tcc tta cac      963
Ala Ile Ala Gln Met Thr Ser Ile Gly Lys Pro Leu Gly Ser Leu His
220                 225                 230                 235 gaa tgg gtt taa acacagttac attactttt ccaattcgtg tttcatgtca          1015
Glu Trp Val aataataatt ttttaaacaa ttatcaatgt tttgtgatat gtttgtaaaa aaaaaaaaa    1075 aaaa                                                                 1079

<210> SEQ ID NO 65
<211> LENGTH: 238
<212> TYPE: PRT
<213> ORGANISM: Renilla muelleri

<400> SEQUENCE: 65

Met Ser Lys Gln Ile Leu Lys Asn Thr Cys Leu Gln Glu Val Met Ser
1               5                   10                  15

Tyr Lys Val Asn Leu Glu Gly Ile Val Asn Asn His Val Phe Thr Met
                20                  25                  30

Glu Gly Cys Gly Lys Gly Asn Ile Leu Phe Gly Asn Gln Leu Val Gln
            35                  40                  45

Ile Arg Val Thr Lys Gly Ala Pro Leu Pro Phe Ala Phe Asp Ile Val
        50                  55                  60

Ser Pro Ala Phe Gln Tyr Gly Asn Arg Thr Phe Thr Lys Tyr Pro Asn
65                  70                  75                  80

Asp Ile Ser Asp Tyr Phe Ile Gln Ser Phe Pro Ala Gly Phe Met Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Asp Lys Phe Val Tyr Arg Val Glu Tyr Lys
        115                 120                 125

Gly Ser Asn Phe Pro Asp Asp Gly Pro Val Met Gln Lys Thr Ile Leu
    130                 135                 140

Gly Ile Glu Pro Ser Phe Glu Ala Met Tyr Met Asn Asn Gly Val Leu
145                 150                 155                 160

Val Gly Glu Val Ile Leu Val Tyr Lys Leu Asn Ser Gly Lys Tyr Tyr
```

```
                    165                 170                 175
Ser Cys His Met Lys Thr Leu Met Lys Ser Lys Gly Val Val Lys Glu
            180                 185                 190

Phe Pro Ser Tyr His Phe Ile Gln His Arg Leu Glu Lys Thr Tyr Val
        195                 200                 205

Glu Asp Gly Gly Phe Val Glu Gln His Glu Thr Ala Ile Ala Gln Met
    210                 215                 220

Thr Ser Ile Gly Lys Pro Leu Gly Ser Leu His Glu Trp Val
225                 230                 235
```

FUSIONS OF SCAFFOLD PROTEINS WITH RANDOM PEPTIDE LIBRARIES

This is a divisional of U.S. patent application Ser. No. 09/415,765, filed Oct. 8, 1999, which is a continuation-in-part of U.S. patent application Ser. No. 09/169,015, U.S. Pat. No. 6,180,343, filed Oct. 8, 1998.

FIELD OF THE INVENTION

The invention relates to the use of scaffold proteins, particularly detectable genes such as green fluorescent protein (GFP), luciferase, β-lactamase, etc., in fusion constructs with random and defined peptides and peptide libraries, to increase the cellular expression levels, decrease the cellular catabolism, increase the conformational stability relative to linear peptides, and to increase the steady state concentrations of the random peptides and random peptide library members expressed in cells for the purpose of detecting the presence of the peptides and screening random peptide libraries. N-terminal, C-terminal, dual N- and C-terminal and one or more internal fusions are all contemplated. Novel fusions utilizing self-binding peptides to create a conformationally stabilized fusion domain are also contemplated.

BACKGROUND OF THE INVENTION

The field of biomolecule screening for biologically and therapeutically relevant compounds is rapidly growing. Relevant biomolecules that have been the focus of such screening include chemical libraries, nucleic acid libraries and peptide libraries, in search of molecules that either inhibit or augment the biological activity of identified target molecules. With particular regard to peptide libraries, the isolation of peptide inhibitors of targets and the identification of formal binding partners of targets has been a key focus. However, one particular problem with peptide libraries is the difficulty assessing whether any particular peptide has been expressed, and at what level, prior to determining whether the peptide has a biological effect.

Green fluorescent protein (GFP) is a 238 amino acid protein. The crystal structure of the protein and of several point mutants has been solved (Ormo et al., Science 273, 1392–5, 1996; Yang et al., Nature Biotechnol. 14, 1246–51, 1996). The fluorophore, consisting of a modified tripeptide, is buried inside a relatively rigid beta-can structure, where it is almost completely protected from solvent access. The fluorescence of this protein is sensitive to a number of point mutations (Phillips, G. N., Curr. Opin. Struct. Biol. 7, 821–27, 1997). The fluorescence appears to be a sensitive indication of the preservation of the native structure of the protein, since any disruption of the structure allowing solvent access to the fluorophoric tripeptide will quench the fluorescence.

Abedi et al (Nucleic Acids Res. 26, 623–30, 1998) have inserted peptides between residues contained in several GFP loops. Inserts of the short sequence (SEQ ID NO:1) between adjacent residues at 10 internal insertion sites were tried. Of these, inserts at three sites, between residues 157–158, 172–173 and 194–195 gave fluorescence of at least 1% of that of wild type GFP. Only inserts between residues 157–158 and 172–173 had fluorescence of at least 10% of wild type GFP. When -SAG-random 20mer-GAS-peptide sequences were inserted at different sites internal to GFP, only two sites gave mean fluorescence intensities of 2% or more of the GFP-random peptide sequences 10-fold above background fluorescence. These sites were insertions between residues 157–158 and 172–173.

It is an object of the invention to provide compositions of fusion constructs of peptides with scaffold proteins, comprising for example detectable proteins such as GFP, and methods of using such constructs in screening of peptide libraries.

SUMMARY OF THE INVENTION

In accordance with the objects outlined above, the present invention provides fusion proteins comprising a scaffold protein and a random peptide, fused to said scaffold protein, and nucleic acids which encode such fusion proteins. In an additional aspect, the present invention provides libraries of: a) fusion proteins; b) fusion nucleic acids; c) expression vectors comprising the fusion nucleic acids; and d) host cells comprising the fusion nucleic acids. The present invention further comprises methods for screening for a bioactive peptide capable of confering a particular phenotype.

In one aspect, a library of fusion proteins comprises a scaffold protein, a random peptide fused to the N-terminus of the scaffold protein and a representation structure that will present the random peptide in a conformationally restricted form. In a preferred embodiment, each of the random peptide in the library is different.

In one aspect, a library of fusion proteins comprises a scaffold protein, a random peptide fused to the C-terminus of the scaffold protein and a representation structure that will present the random peptide in a conformationally restricted form. In a preferred embodiment, each of the random peptide in the library is different.

In one aspect, a library of fusion proteins comprises a scaffold protein, a random peptide inserted into the scaffold protein and at least one fusion partner. In a preferred embodiment, each of the random peptide in the library is different. In another preferred embodiment, the random peptide is inserted into a loop structure of said scaffold protein.

In one aspect of the invention, the scaffold protein is a green fluorescent protein (GFP).

In one aspect of the invention, the GFP is from Aequrea and the random peptide is inserted into the loop comprising amino acids 130 to 135 of said GFP.

In another aspect of the invention, the GFP is from Aequrea and the random peptide is inserted into the loop comprising amino acids 154 to 159 of said GFP.

In another aspect of the invention, the GFP is from Aequrea and the random peptide is inserted into the loop comprising amino acids 172 to 175 of said GFP.

In another aspect of the invention, the GFP is from Aequrea and the random peptide is inserted into the loop comprising amino acids 188 to 193 of said GFP.

In another aspect of the invention, the GFP is from Aequrea and the random peptide is inserted into the loop comprising amino acids 208 to 216 of said GFP.

In one aspect of the invention, the GFP is from a Renilla species.

In another aspect of the invention, the scaffold protein is β-lactamase.

In another aspect of the invention, the scaffold protein is DHFR.

In another aspect of the invention, the scaffold protein is β-galactosidase.

In another aspect of the invention, the scaffold protein is luciferase.

In another aspect of the invention, a library of fusion proteins is provided, comprising a linker between the random peptide and the scaffold protein.

In another aspect of the invention, a library of fusion proteins is provided, comprising a second linker between the other end of the random peptide and the scaffold protein.

In another aspect of the invention, a library of fusion proteins is provided, comprising a -(gly)$_n$- linke, wherein n≧2.

In another aspect of the invention, a library of fusion proteins is provided, comprising a scaffold protein and a random peptide, wherein the random peptide replaces at least one amino acid of said scaffold protein. In a preferred embodiment, the amino acid of said scaffold protein which is replaced by the random peptide is located within a loop structure of said scaffold protein.

In one aspect of the invention, the library of fusion proteins and the library of nucleic acids comprise at least $10^5$ different members.

The invention further provides fusion nucleic acids encoding the fusion proteins. In a preferred embodiment, the nucleic acid encoding the fusion protein comprises a nucleic acid encoding a random peptide, a nucleic acid encoding a scaffold protein and a nucleic acid encoding a fusion partner. In another preferred embodiment, the nucleic acid encoding the random peptide is inserted internally into the nucleic acid encoding the scaffold protein.

In another aspect of the invention, expression vectors are provided. The expression vectors comprise one or more of the nucleic acids encoding the fusion proteins operably linked to regulatory sequences recognized by a host cell transformed with the nucleic acids. In a preferred embodiment the expression vectors are retroviral vectors. Further provided herein are host cells comprising the vectors and the recombinant nucleic acids provided herein.

In a further aspect, the invention provides methods of screening for bioactive peptides conferring a particular phenotype. The methods comprise providing cells containing a fusion nucleic acid comprising nucleic acid encoding a fusion protein comprising a scaffold protein and a random peptide as above. The cells are subjected to conditions wherein the fusion protein is expressed. The cells are then assayed for the phenotype.

Other aspects of the invention will become apparent to the skilled artisan by the following description of the invention.

BRIEF DESCRIPTION OF THE DRAWINGS

FIG. 1 depicts the crystal structure of GFP showing the temperature factors used to pick some of the loops for internal insertion of random peptides.

FIGS. 2A, 2B, 2C, 2D, 2E and 2F (SEQ ID NO:2) depict the results of the examples. FIG. 2A schematically depicts the location of the loops. FIGS. 2B–2F show the results and the mean fluorescence.

FIG. 3 depicts a helical wheel diagram of a parallel coiled coil. For each helix, a or a' are at the N-terminus, and the residues in sequence are abcdefg or a'b'c'd'e'f'g', which are the repeated to give individual helices abcdefg(abcdefg)$_n$abcdefg or a'b'c'd'e'f'g'(a'b'c'd'e'f'g')$_n$a'b'c'd'e'f'g'. The core of the helix would be a, a', d and d', which would be combinations of hydrophobic strong helix forming residues such as ala/leu, or val/leu. If residues e and e' are fixed as glu, and g and g' are fixed as lys, inter-helical salt bridges would further stabilize the coiled coil structure.

FIG. 4 (SEQ ID NO:3) depicts the amino acid sequence of β lactamase TEM-1 from *E.coli*. Amino acid residues 26–290 are shown.

FIGS. 5A and 5B depict the crystal structure of *E. coli* β-lactamase [PDB1 BTL, Jelsch et al., Proteins: Struct., Funct. Genet. 16:364 (19930]. FIG. 5A shows an end-on view of the two helices to which the random library may be fused. FIG. 5B shows a side view of the two helices. The two helices which are to be extended with random residues in this library are shown in yellow (C-terminal helix, containing residues 271–290; see FIG. 4) and white (N-terminal helix, containing residues 2640; see FIG. 4). This protein has residues 1–25 removed. The same residues may be removed in the library scaffold as well. The active site ser 70 is shown in red. Both helices are remote from the active site and therefore attachment of random residues to the N- and/or C-terminus should not affect the activity of the enzyme.

FIG. 6 depicts a model of β-lactamase colored by crystallographic temperature factor, with the most immobile regions shown in red and the more mobile regions in yellow. The loops discussed in Legrande et al. [Nature Biotechnology 17:67–72 (1999)] are shown in blue; the active site ser 70 is shown in white, while glu 166 is shown in blue-gray.

FIG. 7 depicts the structure of Ci-2, taken from the PDB file 2Ci-2. The reactive site loop are represented by residues 54–63; the residues supporting the loop structure are 51, 65, 67, 69 and 83. These residues could be randomized in different combinations. Loop-insert libraries are inserted between residues 72–73 and/or 4445.

FIG. 8 depicts the structure of kanamycin nucleotidyl transferase dimer 1KNY

DETAILED DESCRIPTION OF THE INVENTION

Screening of combinatorial libraries of potential drugs on therapeutically relevant target cells is a rapidly growing and important field. Peptide libraries are an important subset of these libraries. However, to facilitate intracellular screening of these peptide libraries, a number of hurdles must be overcome. In order to express and subsequently screen functional peptides in cells, the peptides need to be expressed in sufficient quantities to overcome catabolic mechanisms such as proteolysis and transport out of the cytoplasm into endosomes. The peptides may also be conformationally stabilized relative to linear peptides to allow a higher binding affinity for their cellular targets. In addition, measuring the expression level of these peptides can be difficult: for example, it may be generally difficult to follow the expression of peptides in specific cells, to ascertain whether any particular cell is expressing a member of the library. To overcome these problems, the present invention is directed to fusions of scaffold proteins, including variants, and random peptides that are fused in such a manner that the structure of the scaffold is not significantly perturbed and the peptide is metabolically conformationally stabilized. This allows the creation of a peptide library that is easily monitored, both for its presence within cells and its quantity. Thus, the peptides within or fused to a scaffold protein are displayed on or at the surface of the scaffold, therefore being accessible for interaction with potential functional targets.

The scaffold proteins fall into two main categories: reporter proteins and structural proteins. Reporter proteins are those that allow cells containing the reporter proteins to be distinguished from those that do not. While determining expression of a particular peptide is difficult, numerous methods are known in the art to measure expression of larger proteins or the expression of genes encoding them. Expression of a gene, e.g., can be measured by measuring the level of the RNA produced. However, this analysis, although direct, is difficult, usually not very sensitive and labor intensive. A more advantageous approach is offered by measuring the expression of reporter genes. Reporter gene expression is generally more easily monitored, since in many cases, the cellular phenotype is altered; either due to the presence of a detectable alterations, such as the presence of a fluorescent protein (which, as outlined herein, includes both the use of fusions to the detectable gene itself, or the use of detectable gene constructs that rely on the presence of the scaffold protein to be activated, e.g. when the scaffold is a transcription factor), by the addition of a substrate altered by the reporter protein (e.g. chromogenic (including fluorogenic) substrates for reporter enzymes such as luciferase, β-galactosidase, etc.), or by conferring a drug resistive phenotype, for example.

Reporter proteins generally fall into one of several classes, including detection genes, indirectly detectable genes, survival genes, etc. That is, by inserting a peptide library into a gene that is detectable, for example GFP or luciferase, the expression of the peptide library may be monitored. Similarly, the insertion of a gene into a survival gene, such as an antibiotic resistance gene, allows detection of the expression of the library.

In some embodiments, it is also desirable for the peptides to have different structural biases, since different protein or other functional targets may require peptides of different specific structures to interact tightly with their surface or crevice binding sites. Thus, different libraries, each with a different structural bias, may be utilized to maximize the chances of having high affinity members for a variety of different targets. Thus, for example, as is more fully outlined below, random peptide libraries with a helical bias or extended structure bias may be made through fusion to the N- terminus and/ or C-terminus of certain scaffold proteins. Similarly, random peptide libraries with a coiled coil bias may be made via fusion to the N- and/or C-terminus of particular scaffold proteins. Extended conformations of the random library may be made using insertions between dimerizing scaffold proteins. Preferred embodiments utilize loop formations via insertion into loops in scaffold proteins; amino acid residues within the respective loop structures may be replaced by the random peptide library or the random peptide library may be inserted in between two amino acid residues located within a loop structure.

Accordingly, the present invention provides fusion proteins of scaffold proteins and random peptides. By "fusion protein" or "fusion polypeptide" or grammatical equivalents herein is meant a protein composed of a plurality of protein components, that while typically unjoined in their native state, typically are joined by their respective amino and carboxyl termini through a peptide linkage to form a single continuous polypeptide. "Protein" in this context includes proteins, polypeptides and peptides. Plurality in this context means at least two, and preferred embodiments generally utilize two components. It will be appreciated that the protein components can be joined directly or joined through a peptide linker/spacer as outlined below. In addition, as outlined below, additional components such as fusion partners including presentation structures, targeting sequences, etc. may be used.

The present invention provides fusion proteins of scaffold proteins and random peptides. By "scaffold protein", "scaffold polypeptide", "scaffold" or grammatical equivalents thereof, herein is meant a protein to which amino acid sequences, such as random peptides, can be fused. The peptides are exogeneous to the scaffold; that is, they are not usually present in the protein. Upon fusion, the scaffold protein usually allows the display of the random peptides in a way that they are accessible to other molecules.

Scaffold proteins fall into several classes, including, reporter proteins (which includes detectable proteins, survival proteins and indirectly detectable proteins), and structural proteins.

In a preferred embodiment, the scaffold protein is a reporter protein. By "reporter protein" or grammatical equivalents herein is meant a protein that by its presence in or on a cell or when secreted in the media allow the cell to be distinguished from a cell that does not contain the reporter protein. As described herein, the cell usually comprises a reporter gene that encodes the reporter protein.

Reporter genes fall into several classes, as outlined above, including, but not limited to, detection genes, indirectly detectable genes, and survival genes.

In a preferred embodiment, the scaffold protein is a detectable protein. A "detectable protein" or "detection protein" (encoded by a detectable or detection gene) is a protein that can be used as a direct label; that is, the protein is detectable (and preferably, a cell comprising the detectable protein is detectable) without further manipulations or constructs. As outlined herein, preferred embodiments of screening utilize cell sorting (for example via FACS) to detect scaffold (and thus peptide library) expression. Thus, in this embodiment, the protein product of the reporter gene itself can serve to distinguish cells that are expressing the detectable gene. In this embodiment, suitable detectable genes include those encoding autofluorescent proteins.

As is known in the art, there are a variety of autofluorescent proteins known; these generally are based on the green fluorescent protein (GFP) from Aequorea and variants thereof; including, but not limited to, GFP, (Chalfie, et al., "Green Fluorescent Protein as a Marker for Gene Expression," Science 263(5148):802–805 (1994)); enhanced GFP (EGFP; Clontech—Genbank Accession Number U55762 )), blue fluorescent protein (BFP; Quantum Biotechnologies, Inc. 1801 de Maisonneuve Blvd. West, 8th Floor, Montreal (Quebec) Canada H3H 1J9; Stauber, R. H. Biotechniques 24(3):462–471 (1998); Heim, R. and Tsien, R. Y. Curr. Biol. 6:178–182 (1996)), and enhanced yellow fluorescent protein (EYFP; Clontech Laboratories, Inc., 1020 East Meadow Circle, Palo Alto, Calif. 94303). In addition, there are recent reports of autofluorescent proteins from Renilla species. See WO 92/15673; WO 95/07463; WO 98/14605; WO 98/26277; WO 99/49019 (e.g., Renilla GFP (SEQ ID NO:64 and SEQ ID NO:65)); U.S. Pat. Nos. 5,292,658; 5,418,155; 5,683,888; 5,741,668; 5,777,079; 5,804,387; 5,874,304; 5,876,995; and 5,925,558; all of which are expressly incorporated herein by reference.

In a preferred embodiment, the scaffold protein is Aequorea green fluorescent protein or one of its variants; see Cody et al., Biochemistry 32:1212–1218 (1993); and Inouye and Tsuji, FEBS Lett. 341:277–280 (1994), both of which are expressly incorporated by reference herein. Accordingly, the present invention provides fusions of green fluorescent protein (GFP) and random peptides. By "green fluorescent protein" or "GFP" herein is meant a protein with at least 30% sequence identity to GFP and exhibits fluorescence at 490 to 600 nm. The wild-type GFP is 238 amino acids in length, contains a modified tripeptide fluorophore buried inside a relatively rigid Scan structure which protects the fluorophore from the solvent, and thus solvent quenching. See Prasher et al., Gene 111(2):229–233 (1992); Cody et al., Biochem. 32(5):1212–1218 (1993); Ormo et al, Science 273:1392–1395 (1996); and Yang et al., Nat. Biotech. 14:1246–1251 (1996), all of which are hereby incorporated by reference in their entirety). Included within the definition of GFP are derivatives of GFP, including amino acid substitutions, insertions and deletions. See for example WO 98/06737 and U.S. Pat. No. 5,777,079, both of which are hereby incorporated by reference in their entirety. Accordingly, the GFP proteins utilized in the present invention may be shorter or longer than the wild type sequence. Thus, in a preferred embodiment, included within the definition of GFP proteins are portions or fragments of the wild type sequence. For example, GFP deletion mutants can be made. At the N-terminus, it is known that only the first amino acid of the protein may be deleted without loss of fluorescence. At the C-terminus, up to 7 residues can be deleted without loss of fluorescence; see Phillips et al., Current Opin. Structural Biol. 7:821 (1997)).

In one embodiment, the GFP proteins are derivative or variant GFP proteins. That is, as outlined more fully below, the derivative GFP will contain at least one amino acid substitution, deletion or insertion, with amino acid substitutions being particularly preferred. The amino acid substitution, insertion or deletion may occur at any residue within the GFP protein. These variants ordinarily are prepared by site specific mutagenesis of nucleotides in the DNA encoding the GFP protein, using cassette or PCR mutagenesis or other techniques well known in the art, to produce DNA encoding the variant, and thereafter expressing the DNA in recombinant cell culture as outlined above. However, variant GFP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the GFP protein amino acid sequence. The variants typically exhibit the same qualitative biological activity as the naturally occurring analogue, although variants can also be selected which have modified characteristics as will be more fully outlined below. That is, in a preferred embodiment, when non-wild-type GFP is used, the derivative preferably has at least 1% of wild-type fluorescence, with at least about 10% being preferred, at least about 50–60% being particularly preferred and 95% to 98% to 100% being especially preferred. In general, what is important is that there is enough fluorescence to allow sorting and/or detection above background, for example using a fluorescence-activated cell sorter (FACS) machine. However, in some embodiments, it is possible to detect the fusion proteins non-fluorescently, using, for example, antibodies directed to either an epitope tag (i.e. purification sequence) or to the GFP itself. In this case the GFP scaffold does not have to be fluorescent; similarly, as outlined below, any of the scaffolds need not be biologically active, if it can be shown that the scaffold is folding correctly and/or reproducibly.

As will be appreciated by those in the art, any of the scaffold proteins or the genes encoding them may be wild type or variants thereof. These variants fall into one or more of three classes: substitutional, insertional or deletional variants. These variants ordinarily are prepared by site specific mutagenesis of nucleotides in the DNA encoding the scaffold protein, using cassette or PCR mutagenesis or other techniques well known in the art, to produce DNA encoding the variant, and thereafter expressing the DNA in recombinant cell culture as outlined herein. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the scaffold protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed scaffold variants screened for the optimal combination of desired activity. Techniques for making substitution mutations at predetermined sites in DNA having a known sequence are well known, for example, M13 primer mutagenesis and PCR mutagenesis. Screening of the mutants is done using assays of scaffold protein activities:

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of a scaffold protein, such as GFP, are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

As outlined above, the variants typically exhibit the same qualitative biological activity (i.e. fluorescence) although variants also are selected to modify the characteristics of the scaffold proteins as needed.

In addition, scaffold proteins can be made that are longer than the wild-type, for example, by the addition of epitope or purification tags, the addition of other fusion sequences, etc., as is more fully outlined below.

In preferred embodiment, the scaffold protein is a variant GFP that has low or no fluorescence, but is expressed in mammalian cells at a concentration of at least about 10 nM, preferably at a concentration of at least about 100 nM, more preferably at a concentration of at least about 1 $\mu$M, even more preferably at a concentration of at least about 10 $\mu$M and most preferred at a concentration of at least about 100 $\mu$M.

A random peptide is fused to a scaffold protein to form a fusion polypeptide. By "fused" or "operably linked" herein is meant that the random peptide, as defined below, and the scaffold protein, as exemplified by GFP herein, are linked together, in such a manner as to minimize the disruption to the stability of the scaffold structure (i.e. it can retain biological activity). In the case of GFP, the scaffold preferably retains its ability to fluoresce, or maintains a Tm of at least 42° C. As outlined below, the fusion polypeptide (or fusion polynucleotide encoding the fusion polypeptide) can comprise further components as well, including multiple peptides at multiple loops, fusion partners, etc.

The fusion polypeptide preferably includes additional components, including, but not limited to, fusion partners and linkers.

In a preferred embodiment, the random peptide is fused to the N-terminus of the GFP. The fusion can be direct, i.e. with no additional residues between the C-terminus of the peptide and the N-terminus of the GFP, or indirect; that is, intervening amino acids are used, such as one or more fusion partners, including a linker. In this embodiment, preferably a presentation structure is used, to confer some conformational stability to the peptide. Particularly preferred embodiments include the use of dimerization sequences.

In one embodiment, N-terminal residues of the GFP are deleted, i.e. one or more amino acids of the GFP can be deleted and replaced with the peptide. However, as noted above, deletions of more than 7 amino acids may render the GFP less fluorescent, and thus larger deletions are generally not preferred. In a preferred embodiment, the fusion is directly to the first amino acid of the GFP.

In a preferred embodiment, the random peptide is fused to the C-terminus of the GFP. As above for N-terminal fusions, the fusion can be direct or indirect, and C-terminal residues may be deleted.

In a preferred embodiment, peptides and fusion partners are added to both the N- and the C-terminus of the GFP. As the N- and C-terminus of GFP are on the same "face" of the protein, in spatial proximity (within 18 Å), it is possible to make a non-covalently "circular" GFP protein using the components of the invention. Thus for example, the use of dimerization sequences can allow a noncovalently cyclized protein; by attaching a first dimerization sequence to either the N- or C-terminus of GFP, and adding a random peptide and a second dimerization sequence to the other terminus, a large compact structure can be formed.

In a preferred embodiment, the random peptide is fused to an internal position of the GFP; that is, the peptide is inserted at an internal position of the GFP. While the peptide can be inserted at virtually any position, preferred positions include insertion at the very tips of "loops" on the surface of the GFP, to minimize disruption of the GFP beta-can protein structure. In a preferred embodiment, loops are selected as having the highest temperature factors in the crystal structure as outlined in the Examples.

In a preferred embodiment, the random peptide is inserted, without any deletion of GFP residues. That is, the insertion point is between two amino acids in the loop, adding the new amino acids of the peptide and fusion partners, including linkers. Generally, when linkers are used, the linkers are directly fused to the GFP, with additional fusion partners, if present, being fused to the linkers and the peptides.

In a preferred embodiment, the peptide is inserted into the GFP, with one or more GFP residues being deleted; that is, the random peptide (and fusion partners, including linkers) replaces one or more residues. In general, when linkers are used, the linkers are attached directly to the GFP, thus it is linker residues which replace the GFP residues, again generally at the tip of the loop. In general, when residues are replaced, from one to five residues of GFP are deleted, with deletions of one, two, three, four and five amino acids all possible. Specific preferred deletions are outlined below. For the structure of GFP, see FIGS. 1 and 2.

Preferred insertion points in loops include, but are not limited to, loop 1 (amino acids 130–135), loop 2 (amino acids 154–159), loop 3 (amino acids 172–175), loop 4 (amino acids 188–193), loop 5 (amino acids 208–216).

Particularly preferred embodiments include insertion of peptides and associated structures into loop 1, amino acids 130–135. In a preferred embodiment, one or more of the loop amino acids are deleted, with the deletion of asp133 being preferred.

In a preferred embodiment, peptides (and fusion partners, if present), are inserted into loop 2, amino acids 154–159. In a preferred embodiment, one or more of the loop amino acids are deleted, with the deletion of both lys156 and gln157 being preferred.

In a preferred embodiment, peptides (and fusion partners, if present), are inserted into loop 3, amino acids 172–175. In a preferred embodiment, one or more of the loop amino acids are deleted, with the deletion of asp173 being preferred.

In a preferred embodiment, peptides (and fusion partners, if present), are inserted into loop 4, amino acids 188–193. In a preferred embodiment, one or more of the loop amino acids are deleted, with the simultaneous deletion of gly189, asp190, gly191, and pro192 being preferred.

In a preferred embodiment, peptides (and fusion partners, if present), are inserted into loop 5, amino acids 208–216. In a preferred embodiment, one or more of the loop amino acids are deleted, with the simultaneous deletion of asn212, glu213 and lys214 being preferred.

In a preferred embodiment, peptides (including fusion partners, if applicable) can be inserted into more than one loop of the scaffold at a time. Thus, for example, adding peptides to both loops 2 and 4 of GFP can increase the complexity of the library but still allow presentation of these loops on the same face of the protein. Similarly, it is possible to add peptides to one or more loops and add other fusion partners to other loops, such as targeting sequences, etc.

Thus, fusion polypeptides comprising GFP and random peptides are provided. In addition, to facilitate the introduction of random peptides into the GFP, a preferred embodiment provides GFP proteins with a multisite cloning site inserted into at least one loop outlined above.

In one embodiment, for example when linkers or other fusion partners are not used, the scaffold may not be GFP.

In a preferred embodiment, the scaffold is a Renilla GFP.

In one embodiment, the scaffold is not Aequorea GFP.

In some embodiments, the scaffold is not any GFP.

In a preferred embodiment, the scaffold protein is an indirectly detectable protein. As for the reporter proteins, cells that contain the indirectly detectable protein can be distinguished from those that do not; however, this is as a result of a secondary event. For example, a preferred embodiment utilizes "enzymatically detectable" scaffolds that comprise enzymes that will act on chromogenic, and particularly fluorogenic, substrates, to generate fluorescence, such as luciferase, β-galactosidase, and β-lactamase. Alternatively, the indirectly detectable protein may require a recombinant construct in a cell that may be activated by the scaffold; for example, scaffold transcription factors or inducers that will bind to a promoter linked to an autofluorescent protein such that transcription of the autofluorescent protein occurs.

In a preferred embodiment, the scaffold is β-lactamase. B-lactamase is generally secreted into the periplasm of bacteria and provides resistance to a variety of penicillins and cephalosporins, including the antibiotic ampicillin. Thus, antibiotic selection of cells comprising a fusion protein of a β-lactamase scaffold with peptide library members allows a determination of library expression. This allows examination of the effects on scaffold folding of different library insertion sites, fusion sites, or library biases by looking at the survival percentage after selection with a β-lactam antibiotic. Usually, eukaryotic β-lactamase libraries have the leader sequence removed to avoid their secretion from the cell. Since β-lactamase is readily assayed using colorimetric reagents [Marshall et al., Diagn. Microbiol. Infect. Dis. 22:353–5 (1995)] or fluorophoric reagents inside a live mammalian cell [Zlokarnik et al., Science 279:84–88 (1998)] the enzyme activity in cell lysates or in live cells allows a ready determination of the fraction of cells which have expressed library members, and cells expressing active β-lactamase library members can be FACS-sorted on the basis of changes in the colorimetric or fluorometric reagents. This enhances the ability to rapidly perform functional screens for peptide library members which alter cell function in a specific fashion.

"β-lactamase" herein includes β-lactamases produced by a variety of microorganisms, including TEM-type extended spectrum β-lactamases (such as from *E. coli*, see below) and class A β-lactamases. β-lactamases within the scope of this invention thus include, but are not limited to TEM-1 β-lactamase from *E. coli*, β-lactamase from *Pseudomonas aeruginosa*, TEM-26B β-lactamase from *Klebsiella oxytoca*, class A β-lactamase from *Capnocytophaga ochracea*, TEM-6 β-lactamase (EC 3.5.2.6) from *E. coli*, TEM-28 β-lactamase from *E. coli*, extended-spectrum β-lactamase TEM-10 from *Morganella morganii*, class A β-lactamase from *Klebsiella pneumoniae*, extended-spectrum β-lactamase CAZ-7 from *Klebsiella pneumoniae*, TEM-3 β-lactamase (EC 3.5.2.6) from *Klebsiella pneumoniae* plasmid. β-lactamases with a high sequence homology to TEM-1 from *E. coli*, especially in the N-and C-terminal helices or in the 84–89 loop, are also preferred.

Accordingly, fusion proteins comprising a β-lactamase scaffold and peptides as outlined below are provided. As for GFP and all the scaffold proteins outlined herein, N-terminal, C-terminal, dual N- and C-terminal and one or more internal fusions, either separately or in combination, are all contemplated.

In a preferred embodiment, internal fusions are preferred. The site of fusion is determined based on the structures of several β-lactamases, which are known; e.g.: β-lactamase from *Bacillus licheniformis* (see Moews et al., Proteins 7(2):156–71 (1990); Knox and Moews, J. Mol. Biol. 220 (2):435–55 (1991)); β-lactamase from *Staphylococcus aureus* (see Herzberg, J. Mol. Biol. 217(4):701–19 (1991); and Chen et al., Biochemistry 35(38):12251–8 (1996)); TEM-1 β-lactamases (see Swaren et al., Biochemistry 38(30):9570–6 (1999); Jelsch et al., Proteins 16(4):364–83 (1993); and Maveyraud et al., Biochemistry 37(8):2622–8 (1998)); class A β-lactamase Toho-1 (see Ibuka et al., J. Mol. Biol. 285(5):2079–87 (1999)); zinc β-lactamase (see Concha et al., Structure 4(7):823–36 (1996)), all of which are expressly incorporated by reference. Insertions of amino acids into loop structures within β-lactamase are especially preferred.

In some embodiments, for example if active β-lactamase enzymatic activity is undesirable in mammalian cells or in bacteria used to test the libraries, such as toxicity to cells or interference with specific functional assays, or to provide an alternative scaffold, the β-lactamase libraries are made using β-lactamase inactivated by site-specific mutations. In the class A β-lactamase PER-1, for example, ala164 would be replaced by arg, or glu166 replaced by ala (see Bouthers et al., Biochem. J. 330:1443–9 (1998)). Likewise, in the TEM-1 β-lactamase, the active site ser70 or glu166 is replaced with ala (Adachi et al., J. Biol. Chem. 266:3186–91 (1991)). In the class A β-lactamase from *B. Licheniformis*, glu166 could be replaced with ala (Knox et al., Protein Eng. 6:11–18 (1993)). As will be appreciated by those in the art, inactive yet folded scaffold proteins, including β-lactamase, may be used.

Active mutants of β-lactamase which are more stable than the wild type enzyme are also preferred as library scaffolds for loop-insert libraries. These mutants can have the advantage that their extra stability enhances the folding of library members with particularly destabilizing random library sequences. Examples of such mutants include E104K and E240K (Raquet et al., Proteins 23:63–72 (1995)). Alternatively, the mutation M182T, which is a global suppressor of missense mutations (Huang and Palzkill, Proc. Natl. Acad. Sci. U.S.A. 94:8801–6 (1997)) may also be included in the scaffold to suppress folding or stability defects resulting in some library members. Again, such reasoning may not only apply for β-lactamase, but for all other enzymes or proteins disclosed herein.

In a preferred embodiment, a derivative of β-lactamase is used as a scaffold protein: N-terminus-BLA-C-terminus, comprising residues 26–290 of *E. coli* TEM-1 β-lactamase, or similar residues of *Staphylococcus aureus* or other β-lactamases (e.g., see FIGS. 5A, 5B, and 6).

In a preferred embodiment, for optimal constraint of a random peptide library, the main site of insertion includes insertion of random amino acids (optionally with linkers and other fusion partners as outlined below) in relative mobile loops which are not close to the active site of the enzyme. FIG. 6 shows a model of β-lactamase depicting the most immobile and mobile regions.

In a preferred embodiment, a preferred loop for insertion of peptide libraries is the loop including I84-D85-A86-G87-Q88-E89 (termed "β-lactamase loop 1" herein), which connects a helix at its N-terminus and an irregular region at its C-terminus. This loop is different from the loops described by Legendre et al. (Nature Biotechnology 17:67–72 (1999)), who specifically selected loops near or affecting the active site to modulate enzyme activity. Here no attenuation of activity is intended or desired.

As outlined above for GFP, one or more loop residues may be replaced or alternatively the insert may be between two residues. In one embodiment, I84, D85 and E89 are fixed in the library since the side chains of each appear to interact with the rest of the β-lactamase structure, although this is not required. Q88 may also optionally be fixed. A86 and G87 may be are replaced, for example with random residues or with random residues flanked by linker residues.

As is further described below, linker amino acids on one or both sides may comprise 2, 3, 4, or more glycines, in order to provide a flexible region between the random library and the rest of the protein. However, as will be appreciated by those in the art, if the loop is mobile enough the linker may not need any glycines. The presence of multiple glycines at least partly conformationally decouples the library from the rest of the protein, enhancing the chances that the library members fold and create active β-lactamase.

In another preferred embodiment, random residues are inserted into alternate loop sites; again, linkers and other fusion partners may optionally be used. Preferred embodiments utilize at least one glycine linker on either side of the random insert to allow a high percentage of β-lactamase-random inserts to fold into active enzyme, due to the relative immobility of the backbone and some of the side chains of the loop.

In a preferred embodiment, loop residues can be replaced or inserted into at positions at D254-G255-K256 ("β-lactamase loop 2"), again with optional linkers, preferably glycine residues, and other fusion partners. In this loop, replacement of the three residues is preferred.

In a preferred embodiment, loop residues can be replaced or inserted into at positions at A227-G228 ("β-lactamase loop 3"), again with optional linkers, preferably glycine residues, and other fusion partners. In this loop, replacement of the two residues is preferred. In some backbones, such as the *Bacillus lichenifirmis* (PDB structure 4BLM) protein, K255-G256-D257 is the loop of choice.

In a preferred embodiment, loop residues can be replaced or inserted into at positions at N52-S53 ("β-lactamase loop 4"), again with optional linkers, preferably glycine residues, and other fusion partners. In this loop, replacement of the two residues is preferred. In some backbones, such as the *Bacillus lichenifirmis* (PDB structure 4BLM) protein, G52-T53-N54 is the loop of choice.

In a preferred embodiment, the random peptide library is fused to the N- or C-terminus of β-lactamase. This optimizes the chances that the scaffold folds well and independently of the sequence of the random peptide library. Such a library with an alpha-helical bias is used e.g., for binding to proteins with binding sites preferring alpha helices, such as leucine zipper proteins, coiled coils, or helical bundles. These helices also act by displacing an existing helix in one of the above structures. To create a bias for a helical structure, the random peptide sequences (chosen from all 20 natural L-amino acids) are fused to the end of a helix which is already nucleated, i.e., which is stable within the native structure and has at least several turns. This can be accomplished by fusion directly to the C-terminal or N-terminal residues of the selected β-lactamases, since both of these termini are extended alpha helices.

In another preferred embodiment the library is strongly biased to an alpha helical structure. In this case the random peptide residues would be composed only of relatively strong helix formers, including M, K, E, A, F, L, R, D, Q, I, or V (e.g., see Lyu et al., Science 250 (4981):669–673 (1990); O'Neil and DeGrado Science 250 (4981):646–651 (1990)].

In another preferred embodiment, mutants of -lactamase are used which include substitutions of P27 in the TEM-1 truncated sequence with any helix-forming amino acid, such as M, K, E, A, F, L, R, D, Q, I, or V.

In a preferred embodiment, the random peptide library is fused to the C-terminus of β-lactamase and the resulting library has the following schematic structure: "N-terminus-BLA-C-terminus-spacer residues-random peptide library-(+/– optional C-cap residues)".

In another preferred embodiment, the random peptide library is fused to the N-terminus of β-lactamase and the resulting library has the following schematic structure: "(+/– optional N-cap residues)-random peptide library-spacer residues-N-terminus-BLA-C-terminus". For cellular expression the first residue would be the strong helix former M.

In a preferred embodiment, 1, 2, 3, 4, 5 or more spacer residues may be inserted between the β-lactamase structure and the random peptide library. In the case of a helix-biased library these spacers may all be strong helix formers, such as M, K, E, A, F, L, R, D, Q, I, or V, in any combination, or in particular sequences such that L and E are 34 residues apart, allowing a side chain salt bridge to further stabilize the helix. The spacers may be charged, so that it would be less likely to be inserted into the interior of the β-lactamase structure.

In a preferred embodiment, the spacer sequence may be KLEALEG, (SEQ ID NO:4) which would bias the sequence to form an alpha helix and interact in a parallel coiled-coil fashion with a helix in a target protein [Monera et al., j. Biol. Chem. 268:19218 (1993)].

In another preferred embodiment, the spacer sequence for β-lactamase C-terminal helix biased libraries may be EEAAKA (SEQ ID NO: 5). Combined with C-terminal wild type sequence -KHW$_{290}$ from *E.coli* TEM-1 β-lactamase, this would give -KHW$_{290}$E$_{291}$E$_{292}$A$_{293}$A$_{294}$K$_{295}$A$_{296}$(SEQ ID NO: 59). E$_{291}$ would be in a position to form an i, i+4 salt bridge with K$_{295}$, and E$_{292}$ could form a similar salt bridge with K$_{288}$. This would stabilize an alpha helix. A$_{293}$A$_{294}$K$_{295}$A$_{296}$ (SEQ ID NO: 60) would form an AXXA motif allowing inserton of a Sfi-I restriction site in the DNA encoding this region, thereby allowing the cloning of random peptide libraries onto the C-terminus of β-lactamase.

In another preferred embodiment, the spacer sequence includes the sequence A$_{292}$E$_{293}$K$_{294}$A$_{295}$K$_{296}$A$_{297}$E$_{298}$, (SEQ ID NO: 61) which would also allow two i, i+4 bridges.

In a preferred embodiment, the scaffold protein is luciferase. The bioluminescent reaction catalyzed by luciferase requires luciferin, ATP, magnesium, and molecular O$_2$. Mixing these components results in a rapidly decaying flash of light which is detected, e.g. by using a luminometer.

In a preferred embodiment, the reporter protein is firefly luciferase [de Wet et al., Mol. Cell. Biol. 7:725–737 (1987); Yang and Thomason, supra; Bronstein et al., supra). Firefly luciferase can also be detected in live cells when soluble luciferase substrates, capable of crossing the plasma membrane are employed (Bronstein et al., supra). The use of firefly luciferase is especially preferred because there is only minimal endogenous activity in mammalian cells.

Luciferases have been cloned from various species and the nucleotide sequences are available (e.g., see GenBank accession numbers E08320, E05448 , D25416, S61961, U51019, M15077, L39928 , L39929, AF085332, U89490, U31240, M10961, M65067, M62917, M25666, M63501, M55977, U03687, and M26194).

In a preferred embodiment, the scaffold protein is *Renilla reniformis* luciferase. Renilla luciferase, DNA encoding Renilla luciferase, and use of the *Renilla reniformis* DNA to produce recombinant luciferase, as well as DNA encoding luciferase from other coelenterates, are well known in the art and are available [see, e.g., SEQ ID No. 1, U.S. Pat. Nos. 5,418,155 and 5,292,658; see also, Prasher et al., Biochem. Biophys. Res. Commun. 126:1259–1268 (1985); Cormier, "Renilla and Aequorea bioluminescence" in Bioluminescence and Chemiluminescence, pp. 225–233 (1981); Charbonneau et al., J. Biol. Chem. 254:769–780 (1979); Ward et al., J. Biol. Chem. 254:781–788 (1979); Lorenz et al., Proc. Natl. Acad. Sci. U.S.A. 88:4438–4442 (1981); Hori et al., Proc. Natl. Acad. Sci. U.S.A. 74:42854287 (1977); Hori et al., Biochemistry 134:2371–2376 (1975); Inouye et al., Jap. Soc. Chem. Lett. 141–144 (1975); and Matthews et al., Biochemistry 16:85–91 (1979)].

As above, fusion proteins comprising luciferase and peptide libraries may be made, at the N-terminus, the C-terminus, both, or one or more internal fusions can be utilized, in combination or alone. The site of fusion may be determined based on the structures of firefly luciferase [Franks et al., Biophys J. 75(5):2205–11 (1998); Conti et al., Structure 4(3):287–98 (1996) luciferase [Fisher et al., Biochemistry 34(20):6581–6 (1995); Fisher et al., J. Biol. Chem. 271(36):21956–68 (1996); Tanner et al., Biochemistry 36(4):665–72 (1997); and Thoden et al., Protein Sci. 6(1):13–23 (1997)], which have been determined. Insertions of amino acids into loop structures within luciferase are especially preferred.

In a preferred embodiment, the scaffold protein is β-galactosidase (Alam and Cook, supra; Bronstein et al., supra). β-galactosidase, encoded by the lacZ gene from *E. coli*, is one of the most versatile genetic reporters and allows both in vitro and in vivo applications. In addition to the *E. coli* lacZ gene, lacZ genes were have been cloned from various species and the nucleotide sequences are available (e.g., see GenBank accession numbers J01636, AB025433, AF073995, U62625, and M57579). The enzyme catalyzes the hydrolysis of several β-galactosides (e.g., Young et al., supra) and is employed in colorimetric assays, e.g., using β-nitrophenyl-β-D-galactopyranoside (ONPG), in chemiluminescent assays based on chemiluminescence of indole (Arakawa et al., J. Biolumin. Chemilumin. 13(6):349–54 (1998)], and in fluorometric assays using e.g., 4-methylumbelliferyl-β-D-galactoside (MUG) and derivatives thereof, such as 6,8-difluoro4-methylumbelliferyl-β-D-galactopyranoside [DiFMUG; Gee et al., Anal. Biochem. 273(1):41–8 (1999)]. Further, the development of chemiluminescent 1,2-dioxetane substrates has greatly improved the sensitivity of detection of enzyme activity. When a luminometer is used to detect the chemiluminescent signal, the assay is 50,000-fold more sensitive than a colorimetric assay. The assay may also be enhanced employing assay conditions that minimize endogenous enzyme activities contributed by eukaryotic β-galactosides (Young et al., supra).

In a preferred embodiment, as for all the scaffolds, β-galactosidase is used in in vivo assays. In vivo assays can be performed in prokaryotic and eukaryotic cells, in tissue sections and intact embryos and includes staining with the precipitating substrate X-gal (Alam and Cook, supra). Further, bioluminescence assays in live cells are employed using fluorescein di-β-D-galactopyranoside (FDG; Bronstein et al., supra). Cells expressing an enzymatically active form of β-galactosidase are detected via fluorescence from the fluorescein moiety of the metabolized substrate.

As above, N-terminal, C-terminal, dual N- and C-terminal and one or more internal fusions, either separately or in combination, are all contemplated. The site of fusion may be determined based on the structure of β-galactosidase, which has been determined [e.g., see Pearl et al., J. Mol. Biol. 229(2):561–3 (1993); Jacobson et al., Nature 369(6483):761–6 (1994); and and Matthews, J. Mol. Biol. 223(4):1177–82 (1992)]. Insertions of amino acids into loop structures within β-galactosidase are especially preferred.

In preferred embodiment, the reporter protein is chloramphenicol acetyltransferase [CAT, Gorman et al., Mol. Cell. Biol., 2:1044–1051 (1982)]. This enzyme catalyzes the transfer of acetyl groups from acetyl-coenzyme A to chloramphenicol. Using CAT as a reporter has the advantage of (i) minimal endogenous activity in mammalian cells, (ii) stable protein expression and (iii) various assay formats are available. The CAT gene has been cloned from various species and the nucleotide sequences are available (e.g., see GenBank accession numbers AF031037, S48276, X74948 , X02872, and M58472).

It is an object of the instant application to fuse amino acid sequences to chloramphenicol acetyltransferase. N-terminal, C-terminal, dual N- and C-terminal and one or more internal fusions are all contemplated. The site of fusion may be determined based on the structure of chloramphenicol acetyltransferase, which has been determined [e.g., see Leslie et al., Proc. Natl. Acad. Sci. U.S. A. 85(12):4133–7 (1988); Lewendon et al., Biochemistry 27(19):7385–90 (1988); and Leslie, J. Mol. Biol. 213(1):167–86 (1990)]. Insertions of amino acids into loop structures within chloramphenicol acetyltransferase are especially preferred.

In a preferred embodiment, the indirectly detectable protein is a DNA-binding protein which can bind to a DNA binding site and activate transcription of an operably linked reporter gene. The reporter gene can be any of the detectable genes, such as green fluorescent protein, or any of the survival genes, outlined herein. The DNA binding site(s) to which the DNA binding protein is binding is (are) placed proximal to a basal promoter that contains sequences required for recognition by the basic transcription machinery (e.g., RNA polymerase II). The promoter controls expression of a reporter gene. Following introduction of this chimeric reporter construct into an appropriate cell, an increase of the reporter gene product provides an indication that the DNA binding protein bound to its DNA binding site and activated transcription. Preferably, in the absence of the DNA binding protein, no reporter gene product is made. Alternatively, a low basal level of reporter gene product may be tolerated in the case when a strong increase in reporter gene product is observed upon the addition of the DNA binding protein, or the DNA binding protein encoding gene. It is well known in the art to generate vectors comprising DNA binding site(s) for a DNA binding protein to be analyzed, promoter sequences and reporter genes.

In a preferred embodiment, the DNA-binding protein is a cell type specific DNA binding protein which can bind to a nucleic acid binding site within a promoter region to which endogenous proteins do not bind at all or bind very weakly. These cell type specific DNA-binding proteins comprise transcriptional activators, such as Oct-2 [Mueller et al., Nature 336(6199):544–51 (1988)] which e.g., is expressed in lymphoid cells and not in fibroblast cells. Expression of this DNA binding protein in HeLa cells, which usually do not express this protein, is sufficient for a strong transcriptional activation of B-cell specific promoters, comprising a DNA binding site for Oct-2 (Mueller et al., supra).

In a preferred embodiment, the indirectly detectable protein is a DNA-binding/transcription activator fusion protein which can bind to a DNA binding site and activate transcription of an operably linked reporter gene. Briefly, transcription can be activated through the use of two functional domains of a transcription activator protein; a domain or sequence of amino acids that recognizes and binds to a nucleic acid sequence, i.e. a nucleic acid binding domain, and a domain or sequence of amino acids that will activate transcription when brought into proximity to the target sequence. Thus the transcriptional activation domain is thought to function by contacting other proteins required in transcription, essentially bringing in the machinery of transcription. It must be localized at the target gene by the nucleic acid binding domain, which putatively functions by positioning the transcriptional activation domain at the transcriptional complex of the target gene.

The DNA binding domain and the transcriptional activator domain can be either from the same transcriptional activator protein, or can be from different proteins (see McKnight et al., Proc. Natl. Acad. Sci. USA 89:7061 (1987); Ghosh et al., J. Mol. Biol. 234(3):610–619 (1993); and Curran et al., 55:395 (1988)). A variety of transcriptional activator proteins comprising an activation domain and a DNA binding domain are known in the art.

In a preferred embodiment the DNA-binding/transcription activator fusion protein is a tetracycline repressor protein (TetR)-VP16 fusion protein. This bipartite fusion protein consists of a DNA binding domain (TetR) and a transcription activation domain (VP16). TetR binds with high specificity to the tetracycline operator sequence, (tetO). The VP16 domain is capable of activating gene expression of a gene of interest, provided that it is recruited to a functional promoter. Employing a tetracycline repressor protein (TetR)-VP16 fusion protein, a suitable eukaryotic expression system which can be tightly controlled by the addition or omission of tetracycline or doxycycline has been described (Gossen and Bujard, Proc. Natl. Acad. Sci. U.S.A. 89:5547–5551; Gossen et al., Science 268:1766–1769 (1995)].

It is an object of the instant application to fuse amino acid sequences to DNA-binding/transcription activator proteins and/or to DNA-binding/transcription activator fusion proteins. N-terminal, C-terminal, dual N- and C-terminal and one or more internal fusions are ll contemplated. The site of fusion may be determined based on the structure of DNA-inding/transcription activator fusion protein, which are determined [e.g., TetR; see Orth et al., J. Mol. Biol. 285(2):455–61 (1999); Orth et al., J. Mol. Biol. 279(2):43947 (1998); Hinrichs et al., Science 264(5157):418–20 (1994); and Kisker et al., J. Mol. Biol. 247(2):260–80 (1995)]. Insertions of amino acids into loop structures within DNA-binding/transcription activator fusion proteins are especially preferred.

In another preferred embodiment the amino acids (=random peptides) are inserted at or close to the fusion site of the DNA binding domain and the transcription activator domain. In this embodiment, a dual scaffold protein is used to present the random peptide library. The random peptide library is such flanked by a scaffold protein representing the DNA binding domain and a scaffold protein representing the transcription activation domain. The random peptide library thus is inserted between the C-terminus of the DNA binding domain and the N-terminus of the transcription activation domain or vice versa. Linker sequences separating the random peptides from the DNA binding domain and transcription activation domain are optional. As indicated by the employment of DNA-binding/transcription activator fusion proteins in protein:protein interaction screening protocols (e.g. see Fields et al., Nature 340:245 (1989); Vasavada et al., Proc. Natl. Acad. Sci. U.S.A. 88:10686 (1991); Fearon et al., Proc. Natl. Acad. Sci. U.S.A. 89:7958 (1992); Dang et al., Mol. Cell. Biol. 11:954 (1991); Chien et al., Proc. Natl. Acad. Sci. U.S.A. 88:9578 (1991); and U.S. Pat. Nos. 5,283,173, 5,667,973, 5,468,614, 5,525,490, and 5,637,463), there is usually significant freedom of amino acid insertion (e.g., a component of a test library) to the DNA binding domain without perturbing either DNA binding or transcription activation.

In a preferred embodiment, the invention provides a composition, comprising (i) a nucleic acid binding site, to which a DNA-binding/transcription activator and/or a DNA binding domain/transcription activator fusion protein can bind, said nucleic acid binding site being operably linked to a reporter gene, (ii) a reporter gene, and (iii) a DNA-binding/transcription activator and/or a DNA binding domain/transcription activator fusion protein which may be encoded by a nucleic acid.

In a preferred embodiment, the scaffold protein is a survival protein. By "survival protein", "selection protein" or grammatical equivalents herein is meant a protein without which the cell cannot survive, such as drug resistance genes. As described herein, the cell usually does not naturally contain an active form of the survival protein which is used as a scaffold protein. As further described herein, the cell usually comprises a survival gene that encodes the survival protein.

The expression of a survival protein is usually not quantified in terms of protein activity, but rather recognized by conferring a characteristic phenotype onto a cell which comprises the respective survival gene or selection gene. Such survival genes may provide resistance to a selection agent (i.e., an antibiotic) to preferentially select only those cells which contain and express the respective survival gene. The variety of survival genes is quite broad and continues to grow (for review see Kriegler, Gene Transfer and Expression: A Laboratory Manual, W.H. Freeman and Company, New York, 1990). Typically, the DNA containing the resistance-conferring phenotype is transfected into a cell and subsequently the cell is treated with media containing the concentration of drug appropriate for the selective survival and expansion of the transfected and now drug-resistant cells.

Selection agents such as ampicillin, kanamycin and tetracycline have been widely used for selection procedures in prokaryotes [e.g., see Waxman and Strominger, Annu. Rev. Biochem. 52:825–69 (1983); Davies and Smith, Annu. Rev. Microbiol. 32:469–518 (1978); and Franklin, Biochem J., 105(1):371–8 (1967)]. Suitable selection agents for the selection of eukaryotic cells include, but are not limited to, blasticidin [Izumi et al., Exp. Cell Res., 197(2):229–33 (1991); Kimura et al., Biochim. Biophys. Acta 1219(3):653–9 (1994); Kimura et al., Mol. Gen. Genet. 242(2):121–9 (1.994)], histidinol D [Hartman and Mulligan; Proc. Natl. Acad. Sci. U.S.A., 85(21):8047–51 (1988)], hygromycin [Gritz and Davies, Gene 25(2–3):179–88 (1983);

Sorensen et al., Gene 112(2):257–60 (1992)], neomycin [Davies and Jimenez, Am. J. Trop. Med. Hyg., 29(5 Suppl) :1089–92 (1980); Southern and Berg, J. Mol. Appl. Genet., 1(4):32741 (19820], puromycin [de la Luna et al., Gene 62(1):121–6 (1988)] and bleomycin/phleomycin/zeocin antibiotics [Mulsant et al., Somat Cell. Mol. Genet. 14(3) :243–52 (1988).

Survival genes encoding enzymes mediating such a drug-resistant phenotype and protocols for their use are known in the art (see Kriegler, supra). Suitable survival genes include, but are not limited to thymidine kinase [TK; Wigler et al., Cell 11:233 (1977)], adenine phosphoribosyltransferase [APRT; Lowry et al., Cell 22:817 (1980); Murray et al., Gene 31:233 (1984); Stambrook et al., Som. Cell. Mol. Genet. 4:359 (1982)], hypoxanthine-guanine phosphoribosyltransferase [HGPRT; Jolly et al., Proc. Natl. Acad. Sci. U.S.A. 80:477 (1983)], dihydrofolate reductase [DHFR; Subramani et al., Mol. Cell. Biol. 1:854 (1985); Kaufman and Sharp, J. Mol. Biol. 159:601 (1982); Simonsen and Levinson, Proc. Natl. Acad. Sci. U.S.A. 80:2495 (1983) ] aspartate transcarbamylase [Ruiz and Wahl, Mol. Cell. Biol. 6:3050 (1986)], ornithine decarboxylase [Chiang and McConlogue, Mol. Cell. Biol. 8:764 (1988)], aminoglycoside phosphotransferase [Southern and Berg, Mol. Appl. Gen. 1:327 (1982); Davies and Jiminez, supra], hygromycin-B-phosphotransferase [Gritz and Davies, supra; Sugden et al., Mol. Cell. Biol. 5:410 (1985); Palmer et al., Proc. Natl. Acad. Sci. U.S.A. 84:1055 (1987)], xanthine-guanine phosphoribosyltransferase [Mulligan and Berg, Proc. Natl. Acad. Sci. U.S.A. 78:2072 (1981)], tryptophan synthetase [Hartman and Mulligan, Proc. Natl. Acad. Sci. U.S.A. 85:8047 (1988)], histidinol dehydrogenase (Hartman and Mulligan, supra), multiple drug resistance biochemical marker [Kane et al., Mol. Cell. Biol. 8:3316 (1988); Choi et al., Cell 53:519 (1988)], blasticidin S deaminase [Izumi et al., Exp. Cell. Res. 197(2):229–33 (1991)], bleomycin hydrolase [Mulsant et al., supra], and puromycin-N-acetyl-transferase [Lacalle et al., Gene 79(2):375–80 (1989)].

In a preferred embodiment, the survival protein is thymidine kinase [TK; Wigler et al., Cell 11:233 (1977)]. TK is encoded by the HSV or vaccinia virus tk genes. When transferred into a TK$^-$ cell, these genes confer resistance to HAT medium, a medium supplemented with hypoxanthine, aminopterin and thymidine. TKs have been cloned from various species and the nucleotide sequences are available (e.g., see GenBank accession numbers M29943, M29942, M29941 and K02611).

It is an object of the instant application to fuse amino acid sequences to thymidine kinase. N-terminal, C-terminal, dual N- and C-terminal and one or more internal fusions are all contemplated. The site of fusion may be determined based on the structures of HSV thymidine kinase, which has been determined [e.g., see Bennett et al., FEBS Lett. 443(2) :121–5 (1999); Champness et al., Proteins 32(3):350–61 (1998); and Brown et al., Nat. Struct. Biol. 2(10):876–81 (1995)]. Insertions of amino acids into loop structures within thymidine kinase are especially preferred.

In another preferred embodiment, the survival protein is adenine phosphoribosyltransferase [APRT; Lowry et al., Cell 22:817 (1980); Murray et al., Gene 31:233 (1984); Stambrook et al., Som. Cell. Mol. Genet. 4:359 (1982)]. When transferred into a APRT$^-$ cells, the gene encoding APRT confers resistance to complete medium, supplemented with azaserine, adenine and alanosine. APRT genes have been cloned from various species, including human, and the nucleotide sequences are available (e.g., see GenBank accession numbers L25411, AF060886, X58640, U16781, U22442, U28961, L06280, M16446, L04970, and M11310).

It is an object of the instant application to fuse amino acid sequences to adenine phosphoribosyltransferase. N-terminal, C-terminal, dual N- and C-terminal and one or more internal fusions are all contemplated. The site of fusion may be determined based on the structures of adenine phosphoribosyltransferase from Leishmania donovani, which has been determined [Phillips et al., EMBO J. 18(13) :353345 (1999)]. Insertions of amino acids into loop structures within adenine phosphoribosyltransferase are especially preferred.

In a preferred embodiment, the survival protein is hypoxanthineguanine phosphoribosyltransferase [HGPRT; Jolly et al., Proc. Natl. Acad. Sci. U.S.A. 80:477 (1983)]. When transferred into a HGPRT$^-$, APRT$^-$ cells, the gene encoding HGPRT confers resistance to HAT medium. HGPRT genes have been cloned from various species, including human, and the nucleotide sequences are available (e.g., see GenBank accession numbers AF170105, AF061748 , L07486, J00423, M86443, J00060, and M26434).

It is an object of the instant application to fuse amino acid sequences to hypoxanthineguanine phosphoribosyltransferase. N-terminal, C-terminal, dual N- and C-terminal and one or more internal fusions are all contemplated. The site of fusion may be determined based on the structures of human hypoxanthine-guanine phosphoribosyltransferase, which has been determined [Shi et al., Nat. Struct. Biol. 6(6):588–93); Eads et al., Cell 78(2):325–34 (1994)]. Insertions of amino acids into loop structures within hypoxanthine-guanine phosphoribosyltransferase are especially preferred.

In a preferred embodiment, the survival protein is dihydrofolate reductase (DHFR), which is encoded by the dhfr gene [Subramani et al., Mol. Cell. Biol. 1:854 (1985); Kaufman and Sharp, J. Mol. Biol. 159:601 (1982); Simonsen and Levinson, Proc. Natl. Acad. Sci. U.S.A. 80:2495 (1983)]. When transferred into a DHFR- cells, the gene encoding DHFR confers resistance to medium containing methotrexate. DHFR genes have been cloned from various species, including human, and the nucleotide sequences are available (e.g., see GenBank accession numbers NM_000791, J01609, J00140, L26316, and M37124).

It is an object of the instant application to fuse amino acid sequences to dihydrofolate reductases. N-terminal, C-terminal, dual N- and C-terminal and one or more internal fusions are all contemplated. The site of fusion may be determined based on the structures of human and *E. coli* dihydrofolate reductases, which have been determined [Cody et al., Biochemistry 36(45):13897–903 (1997); Chunduru et al., J. Biol. Chem. 269(13):9547–55 (1994); Lewis et al., J. Biol. Chem. 270(10):5057–64 (1995); Sawaya et al., Biochemistry 36(3):586–603 (1997); Reyes et al., Biochemistry 34(8):2710–23 (1995)]. Insertions of amino acids into loop structures within dihydrofolate reductases are especially preferred.

In a preferred embodiment, the survival protein is aspartate transcarbamylase. Aspartate transcarbamylase is encoded by pyrB [Ruiz and Wahl, Mol. Cell. Biol. 6:3050 (1986)]. When transferred to CHO D2O (UrdA mutant; deficient in the first three enzymatic activities of de novo uridine biosynthesis: carbamyl phosphate synthetase, aspartate transcarbamylase, and dihydroorotase )the gene encoding this protein confers resistance to Ham F-12 medium (minus uridine). Aspartate transcarbamylase genes have been cloned from various species, including human, and the nucleotide sequences are available (e.g., see GenBank accession numbers U61765, M38561, J04711, M60508 , and M13128).

It is an object of the instant application to fuse amino acid sequences to aspartate transcarbamylase. N-terminal, C-terminal, dual N- and C-terminal and one or more internal fusions are all contemplated. The site of fusion may be determined based on the structures of E.coli aspartate transcarbamylase, which has been determined [Kantrowitz and Lipscomb, Science 241(4866):669–74 (1988)]. Insertions of amino acids into loop structures within aspartate transcarbamylase are especially preferred.

In a preferred embodiment, the survival protein is ornithine decarboxylase. Ornithine decarboxylase is encoded by the odc gene [Chiang and McConlogue, Mol. Cell. Biol. 8:764 (1988)]. When transferred into CHO C55.7 cells (ODC⁻) the gen encoding this protein confers resistance medium lacking putrescine. ODC genes have been cloned from various species, including human, and the nucleotide sequences are available (e.g., see GenBank accession numbers U36394, AF016891, AF012551, U03059, J04792, and M34158).

It is an object of the instant application to fuse amino acid sequences to ornithine decarboxylase. N-terminal, C-terminal, dual N- and C-terminal and one or more internal fusions are all contemplated.

In a preferred embodiment, the survival protein is aminoglycoside phosphotransferase, which is encoded by the aph gene [Southern and Berg, Mol. Appl. Gen. 1:327 (1982); Davies and Jiminez, supra]. When transferred into almost any cell, this dominant selectable gene confers resistance to G418 (neomycin, geneticin). Aminoglycoside phosphotransferase encoding genes have been cloned and used widely as a selectable marker on various vectors (e.g., see GenBank accession numbers Z48231, M22126, U75992, AF072538 , and U04894).

It is an object of the instant application to fuse amino acid sequences to aminoglycoside phosphotransferase. N-terminal, C-terminal, dual N- and C-terminal and one or more internal fusions are all contemplated.

In a preferred embodiment, the survival protein is hygromycin-B-phosphotransferase, which is encoded by the hph gene [Gritz and Davies, supra; Sugden et al., Mol. Cell. Biol. 5:410 (1985); Palmer et al., Proc. Natl. Acad. Sci. U.S.A. 84:1055 (1987)]. When transferred into almost any cell, this dominant selectable gene confers resistance to hygromycin-B. The hygromycin-B-phosphotransferase encoding gene has been cloned and used widely as a selectable marker on various vectors (e.g., see GenBank accession numbers AF025747, L76273, and K01 193).

It is an object of the instant application to fuse amino acid sequences to hygromycin-B-phosphotransferase. N-terminal, C-terminal, dual N- and C-terminal and one or more internal fusions are all contemplated.

In another preferred embodiment, the survival protein is xanthine-guanine phosphoribosyltransferase, which is encoded by the gpt gene [Mulligan and Berg, Proc. Natl. Acad. Sci. U.S.A. 78:2072 (1981)]. When transferred into almost any cell, this dominant selectable gene confers resistance to XMAT medium, comprising xanthine, hypoxanthine, thymidine, aminopterin, mycophenolic acid and L-glutamine. The xanthine-guanine phosphoribosyltransferase encoding gene has been cloned and the nucleotide sequences are available (e.g., see GenBank accession numbers U28239 and M15035).

It is an object of the instant application to fuse amino acid sequences to xanthine-guanine phosphoribosyltransferase. N-terminal, C-terminal, dual N- and C-terminal and one or more internal fusions are all contemplated.

In another preferred embodiment, the survival protein is tryptophan synthetase, which is encoded by the trpB gene [Hartman and Mulligan, Proc. Natl. Acad. Sci. U.S.A. 85:8047 (1988)]. When transferred into almost any cell, this dominant selectable gene confers resistance to tryptophan-minus medium. Tryptophan synthetase encoding genes have been cloned and the nucleotide sequences are available (e.g., see GenBank accession numbers V00372, AF173835, V00365, M15826 and M32108).

It is an object of the instant application to fuse amino acid sequences to tryptophan synthetase. N-terminal, C-terminal, dual N- and C-terminal and one or more internal fusions are all contemplated. The site of fusion may be determined based on the structure of tryptophan synthetase, which has been determined [e.g., see Rhee et al., Biochemistry 36(25):7664–80 (1997); Hyde et al., J. Biol. Chem. 263(33):17857–71 (1988)]. Insertions of amino acids into loop structures within tryptophan synthetase are especially preferred.

In a further preferred embodiment, the survival protein is histidinol dehydrogenase, which is encoded by the hisD gene [Hartman and Mulligan, Proc. Natl. Acad. Sci. U.S.A. 85:8047 (1988)]. When transferred into almost any cell, this dominant selectable gene confers resistance to media comprising histidinol. Histidinol dehydrogenase encoding genes have been cloned and the nucleotide sequences are available (e.g., see GenBank accession numbers AB013080, U82227, J01804, and M60466).

It is an object of the instant application to fuse amino acid sequences to histidinol dehydrogenase. N-terminal, C-terminal, dual N- and C-terminal and one or more internal fusions are all contemplated.

In another preferred embodiment, the survival protein is the multiple drug resistance biochemical marker, which is encoded by the mdri gene [Kane et al., Mol. Cell. Biol. 8:3316 (1988); Choi et al., Cell 53:519 (1988)]. When transferred into almost any cell, this dominant selectable gene confers resistance to media comprising colchicine. MDR1 genes have been cloned from various species, including human, and the nucleotide sequences are available (e.g., see GenBank accession numbers U62928 , U62930, AJ227752, U62931, AF016535 and J03398).

It is an object of the instant application to fuse amino acid sequences to MDR1. N-terminal, C-terminal, dual N- and C-terminal and one or more internal fusions are all contemplated.

In another preferred embodiment, the survival protein is blasticidin S deaminase, which is encoded by the bsr gene [Izumi et al., Exp. Cell. Res. 197(2):229–33 (1991)]. When transferred into almost any cell, this dominant selectable gene confers resistance to media comprising the antibiotic blasticidin S. Blasticidin S deaminase encoding genes have been cloned. They are used widely as a selectable marker on various vectors and the nucleotide sequences are available (e.g., see GenBank accession numbers D83710, U75992, and U75991).

It is an object of the instant application to fuse amino acid sequences to blasticidin S deaminase. N-terminal, C-terminal, dual N- and C-terminal and one or more internal fusions are all contemplated. The site of fusion may be determined based on the structure of Aspergillus terreus blasticidin S deaminase, which has been determined [Nakasako et al., Acta Crystallogr. D. Biol. Crystallogr. 55(Pt2):547–8 (1999)]. Insertions of amino acids into loop structures within blasticidin S deaminase are especially preferred.

In another preferred embodiment, the survival protein is bleomycin hydrolase, which is encoded by the ble gene [Mulsant et al., supra]. When transferred into almost any cell, this dominant selectable gene confers resistance to media comprising bleomycin, phleomycin or zeocin. Bleomycin hydrolase encoding genes have been cloned. They are used widely as a selectable marker on various vectors and the nucleotide sequences are available (e.g., see GenBank accession numbers L26954, L37442, and L36849).

It is an object of the instant application to fuse amino acid sequences to bleomycin hydrolase. N-terminal, C-terminal, dual N- and C-terminal and one or more internal fusions are all contemplated. The site of fusion may be determined based on the structure of yeast (Gal6) and human bleomycin hydrolase, which have been determined [Joshua-Tor et al., Science 269(5226):945–50 (1995); O'Farrell et al., Structure Fold. Des. 7(6):619–27 (1999)]. Insertions of amino acids into loop structures within bleomycin hydrolase are especially preferred.

In another preferred embodiment, the survival protein is puromycin-N-acetyl-transferase, which is encoded by the pac gene [Lacalle et al., Gene 79(2):375–80 (1989)]. When transferred into almost any cell, this dominant selectable gene confers resistance to media comprising puromycin. A puromycin-N-acetyltransferase encoding gene has been cloned. It is used widely as a selectable marker on various vectors and the nucleotide sequences are available (e.g., see GenBank accession numbers Z75185 and M25346).

It is an object of the instant application to fuse amino acid sequences puromycin-N-acetyl-transferase. N-terminal, C-terminal, dual N- and C-terminal and one or more internal fusions are all contemplated.

In another preferred embodiment, the scaffold protein is a structural protein. In this embodiment, the scaffold protein is generally not directly detectable, but is generally a small, stable, non-disulfide bond-containing protein.

In a preferred embodiment, the presentation scaffold significantly constrains the presented random peptides. The peptides will be conformationally pre-constrained, will have a diminished number of low energy conformers, and will thus lose less entropy when bound to a target binding partner (a macromolecule such as a protein, DNA, or other functional molecule present within or on the outside of a cell). Such constrained peptides may thus bind more tightly to a target molecule than unconstrained peptides. Likewise, constrained peptides may be less subject to intracellular catabolism than unconstrained peptides, especially by proteases. Different scaffold may impart different biases to peptides depending on the insertion site of the random peptide libraries.

In a preferred embodiment, the scaffold comprises protease inhibitors belonging to the trypsin inhibitor I family, such as barley chymotrypsin inhibitor 2 (Ci-2) and eglin C. Both of these proteins are small (83 and 64 residues, respectively), stable, and lack disulfide bonds, thus allowing their expression and folding in the cytoplasm of a mammalian cell without the complications of disulfide bond formation. Disulfide bond formation is difficult in the cytoplasm due to high levels of reduced glutathione, and the presence of thioredoxin reductase. The folding mechanism of Ci-2 has been studied in detail, implying a two-state process with the rate limiting step for two slow phases being proline isomerization [Jackson and Fersht, Biochemistry 30:10428–35 (1991)]. It has been shown to refold when cleaved into two separate pieces, composed of residues 20–59 and 60–83, with the fragments associating to form a native-like structure with a $K_d$ of 42 nM [de Prat Gay and Fersht, Biochemistry 33:7957–63 (1994)]. Ci-2 blocks subtilisin BPN' with an inhibition constant of 2.9 pM [Longstaff et al., Biochemistry 29:733947 (1990)].

In a preferred embodiment, Ci-2 and the similar protease inhibitor eglin-C are used as scaffolds for a small protein-embedded random peptide library. Since different intracellular targets demand bound peptides of different conformations, it is important to construct peptide libraries with different biases, as already outlined above. The crystal structure of Ci-2 [see FIG. 7 and McPhalen and James, Biochemistry 26:261–269 (1987)] allows the construction of a different random peptide library with an additional bias: a broad-based 20A constraint, with both ends fixed at this distance by the Ci-2 scaffold. There are at least three random peptide library insertion sites that may result in libraries with useful properties. At each insertion site, the use of a varying number of inserted residues affect the conformational bias of the peptide library and thus creates a set of libraries.

In a preferred embodiment, the insertion site replaces the Ci-2 inhibitor loop residues G54-R62 with 9 or more random amino acids. Inserting 9 random residues to replace the 9 existing residues in G54-R62 will bias the library to a broad-based semicircular loop, roughly 20 Å at its base. Inserting more residues will bias the library to more flexible peptides. Inserting correspondingly more residues in a slightly larger insertion site in this inhibitor loop, e.g., inserting 13 residues between 52 and 64, will create a library with a bias towards the top ca. 2/3 of a large ca. 18mer cyclic peptide. A library replacing all ~19 residues of this nearly circular loop (residues 49–67) will in effect mimic a large 19 residue cycle peptide and thus would be different than any of the above libraries.

In a preferred embodiment, the above libraries substituting G54-R62, are made more flexible by substituting random residues for native residues at the base of this inhibitor loop which appear to support the top of the loop. Without this support, the top residues may be significantly more flexible. The supporting residues appear to include F69, L51, R67, and R65. G83 could also be randomized since it is near the side of the loop in the crystal structure.

In another preferred embodiment, the random peptide library is inserted between K72-L73 of Ci-2.

In another preferred embodiment, the random peptide library replaces residues P44-E45 of Ci-2.

Insertion of a random peptide library between residues K72-L73 or replacing residues P44-E45 will lead to different libraries, roughly biased to a loop with a closed or short base, but in a much smaller protein scaffold (9 kDa) than e.g., GFP (27 kDa) or DHFR (20 kDa). Therefore, these two libraries may be useful as small loop-biased libraries.

In a preferred embodiment, random peptide libraries between residues K72-L73 or random peptide libraries replacing residues P44-E45 may be used as selectable libraries, allowing the elimination of cells not expressing a properly folded and bioactive library member, or of uninfected cells. When a random peptide libraries is inserted between residues K72-L73 or replacing residues P44-E45, use of the still-active protease inhibitor residues in positions ca. 54–62 should retain the ability to inhibit subtilisin BPN', and thus to select cells co-expressing a properly folded inhibitor library member and a cognate inhibitable protease such as subtilisin BPN', $K_i$=2.9 pM (Longstaff, supra). The selection, thus would be by protection against protease-induced cell death at an appropriate time point after infection or transfection of the cells with the Ci-2 library.

In another preferred embodiment, analogous library insertion sites may be used with eglin-C or other potato trypsin inhibitor I family members lacking disulfide bonds, which have similar structures to that of Ci-2.

In a preferred embodiment, the fusion protein comprising the scaffold protein and the random peptide library is bioactive, e.g., has enzymatic activity. However, as outlined herein, the fusion protein need not display such a bioactive function. A preferred property of the fusion protein is, however, to present the random peptide sequences to potential binding partners.

In a preferred embodiment, multiple scaffolds are used for the intracellular (and extracellular) presentation of peptide libraries with a bias to extended peptides. Extended conformations are important for molecular recognition in a number of peptide-protein complexes [Siligardi and Drake, Biopolymers 37(4)281–92 (1995)] including peptide substrate (and inhibitor) binding to a large variety of proteases, kinases and phosphatases, peptide binding to MHC class I and II proteins, peptide binding to chaperones, peptide binding to DNA, and B cell epitopes. Additional examples of extended bound peptides include a troponin inhibitory peptide binding to troponin C [Hernanderz et al., Biochemistry 38:6911–17 (1999)] and a p21-derived peptide binding to PCNA [Gulbis et al., Cell 87:297–306 (1996)]. Linear peptides are a unique secondary structure and thus appear important in a number of peptide-protein binding interactions.

The intracellular catabolism of peptides is one limiting factor which may prevent significant steady state levels of small peptides. Proteases, such as aminopeptidases [Lee and Goldberg, Biopolymers 37:281–92 (1992)] as well as carboxypeptidases and the proteasome, as outlined further below, may be involved in the degradation of intracellular peptides. Thus, linear or extended peptides may be readily degraded after their intracellular expression In a preferred embodiment, the library is constructed allowing the random library members, consisting of 18–30 random residues, to have linear/extended configurations without both free N-termini (allowing aminopeptidase-mediated degradation) and free C-termini (allowing carboxypeptidase-mediated degradation). In this embodiment, the scaffold present the random peptides with a linear/extended structural bias (but not as an absolute requirement) and allow significant peptide flexibility while somewhat limiting intracellular catabolism. Fusion of proteins to both ends of the library should protect the random sequences from amino- and carboxy-peptidases.

Accordingly, in a preferred embodiment, a dual fusion scaffold fusion protein of the following form is constructed: N-terminus-protein 1-linker 1-random peptide library-linker 2-protein 2-C-terminus.

In a preferred embodiment, protein 1 and protein 2 are the same protein. Alternatively, protein 1 and protein 2 are different proteins.

In a preferred embodiment, linker 1 and linker 2 are the same linker. Alternatively, linker 1 and linker 2 are different linkers.

In a preferred embodiment, protein 1 and protein 2 are selected from a group of proteins which have low affinity for each other.

In another preferred embodiment, protein 1 and protein 2 are selected from a group of proteins that are well-expressed in mammalian cells or in the cell in which the random peptide library is tested. Included in this embodiment are proteins with a long intracellular half-life, such as CAT and others known in the art.

In another preferred embodiment, protein 2 is a selection protein, such as DHFR or any other, as either outlined above or known in the art. In this embodiment, selection of full-length library members in mammalian cells or in cells in which the library is tested can be achieved. Selection procedures were outlined above. Alternatively, protein 1 is a selection protein.

In another preferred embodiment, protein 2 is a reporter protein, such as GFP or any other fluorescent protein, β-lactamase, another highly colored protein, as either outlined above or known in the art. In this embodiment, intracellular detection and tracking of full-length library members in mammalian cells or in cells in which the library is tested can be achieved. Reporter-gene product analyses were outlined above. Alternatively, protein 1 is a reporter protein.

In another preferred embodiment, protein 1 is a reporter protein and protein 2 is a selection protein, allowing, both intracellular tracking and selection of full-length library member.

Linker 1 and linker 2 should not have a high self-affinity or a noncovalent affinity for either protein 1 or protein 2.

In a preferred embodiment, linker 1 and/or linker 2 consist(s) of residues with one or more glycines to decouple the structure from protein 1 and protein 2 from the random library.

In another preferred embodiment, linker 1 and or linker 2 provide(s) enough residues which, when extended, provide 0.5–1 protein diameter spacing between the random residues and proteins 1 and 2. This would correspond to approximately 15–30 Å or 5–10 residues and would minimize steric interference in peptide library member binding to potential targets.

In another preferred embodiment, linker 1 and/or linker 2 contain(s) enough hydrophilic residues so that the linkers do not adversely affect the solubility or stickiness of the entire fusion protein or of the linker region alone.

In another preferred embodiment, a relatively rigid structure can be formed from the linkers to force the random residues away from the surfaces of proteins 1 and 2.

In a preferred embodiment, the cellular protein p21 is used to display a linear peptide to binding partners. The tumor suppressor protein p21 binds to PCNA via its C-terminal 22 residues by effectively displaying this C-terminal peptide to PCNA in an extended conformation (Gulbis et al., supra). Therefore this scaffold may be useful for the display of random peptide libraries with an extended structural bias in the position of some or all of the C-terminal 22 residues, with the C-terminal residues now being randomized. The structure of the p21 scaffold appears to be disordered and to become more ordered at its N-terminus upon binding to cyclin-dependent kinases (CDKs). The overall disordered structure may suggest that this scaffold nay be particularly useful for displaying extended (disordered) peptide libraries.

In a preferred embodiment, the nuclear localization sequence of p21, located between residues 141 and 156 is deleted and replaced by random residues. The random peptide library is thus inserted that it replaces the nuclear localization signal. Thereby this scaffold should function as a scaffold for a cytoplasmic peptide library. By remaining in the cytoplasm, the p21 scaffold library members should not bind to nuclear cyclins and CDKs and thus should not perturb the cell cycle.

To ensure deletion of p21 functions such as inhibition of CDKs, in case low levels of the peptide library members enter the nucleus, the appropriate domains can be inactivated by site-directed mutagenesis, as known in the art. One such mutation, R94W, blocks the ability of p21 to inhibit cyclin-dependent kinases [Balbin et al., J. Biol. Chem. 271:15782–6 (1996)]. A second mutant in a p21 CDK- construct, also blocking CDK binding, has been shown to stabilize p21 to proteosomal degradation [Cayrol and Ducommun, Oncogene 17:243744 (1998)] and thus may be preferred as a scaffold. A third mutant, N50S also blocks CDK inhibition by p21 [Welcker et al., Cancer Res. 58:5053–6 (1998)]. Alternatively, the cy-1 site (residues 17–24) may be deleted, blocking both cyclin- and cyclin-CDK complex binding to p21 [Chen et al., Mol. Cell. Biol. 16:4673–82 (1996)]. The cy-2 cyclin binding site, at residues 152–158, may also be deleted in case the random library is inserted in place of residues 141–164.

In another preferred embodiment the scaffold protein is kanamycin nucleotidyl transferase (see FIG. 8). Kanamycin nucleotidyl transferase forms tight dimers. In this embodiment, the extended-bias random peptides would be inserted between the C-terminus of the first dimer and the N-terminus of the second dimer, with spacer residues between each protein and the random residues. The spacer residues on either side of the random library region would consist of at least 5–10 residues on each side of the random peptide library, including one or more glycines and no hydrophobic residues.

The fusion proteins of the present invention comprise a scaffold protein and a random peptide. The peptides (and nucleic acids encoding them) are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. As is more fully described below, the nucleic acids which give rise to the peptides are chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids.

The library should provide a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is necessary for completion of the signaling pathway. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, for example, with libraries of $10^7$ to $10^8$ per ml of retroviral particles the present methods allow a "working" subset of a theoretically complete interaction library for 7 amino acids, and a subset of shapes for the $20^{20}$ library.

Thus, in a preferred embodiment, at least $10^5$, preferably at least $10^6$, more preferably at least $10^7$, still more preferably at least $10^8$ and most preferably at least $10^9$ different peptides may be simultaneously analyzed as outlined herein.

Thus, a library of fusion proteins, each fusion protein comprising a scaffold protein and a random peptide, comprises at least $10^5$, preferably at least $10^6$, more preferably at least $10^7$, still more preferably at least $10^8$ and most preferably at least $10^9$ different random peptides.

In another preferred embodiment, an indivdual member of the library of fusion proteins, is analyzed as outlined herein. Alternatively, more than one individual member of the library of fusion proteins may be simultaneously analyzed.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3164, or 4.69%, chance that the codon will be a stop codon. Thus, in a peptide of 10 residues, there is an unacceptable high likelihood that 46.7% of the peptides will prematurely terminate. For free peptide structures this is perhaps not a problem. But for larger structures, such as those envisioned here, such termination will lead to sterile peptide expression. To alleviate this, random residues are encoded as NNK, where K=T or G. This allows for encoding of all potential amino acids (changing their relative representation slightly), but importantly preventing the encoding of two stop residues TAA and TGA. Thus, libraries encoding a 10 amino acid peptide will have a 15.6% chance to terminate prematurely. However, it should be noted that the present invention allows screening of libraries containing terminated peptides in a loop, since the GFP will not fluoresce and thus these peptides will not be selected.

In a preferred embodiment, the peptide library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

For example, individual residues may be fixed in the random peptide sequence of the insert to create a structural bias, similar to the concept of presentation structures outlined below. A preferred embodiment utilizes inserts of a general structure -gly$_{2-8}$-aa$_1$-aa$_2$- . . . -aa$_n$-gly$_{2-8}$- where the random insert sequence is aa$_1$ to aa$_n$. This sequence can be constrained by fixing one or more of the n residues as prolines (which will significantly restrict the conformation space of the entire loop), as bulky amino acids such as W, R, K, L, I, V, F, or Y, or biasing the set of random amino acids to include only bulky residues such as E, F, H, I, K, L, M, Q, R, T, V, W, and Y. Due to the larger size of the side chains, these residues will have fewer ways to pack into a small space that is defined by that available to a loop, and thus there will be fewer available loop conformations.

In an alternative embodiment, the random libraries can be biased to a particular secondary structure by including an appropriate number of residues (beyond the glycine linkers) which prefer the particular secondary structure. For example, to create an alpha-helical bias the entire loop insert might look like -gly$_{2-4}$-helix former $_{4-8}$-random residues-helix former $_{4-8}$-gly$_{2-8}$-, where the 4–8 helix formers at each end of the randomized region will nucleate an alpha helix and raise the probability that the random inserts will be helical; to further this bias, the randomized region can be devoid of strong helix breakers such as pro and gly; examples of strong helix forming residues would include M, A, K, L, D, E, R, Q, F, I and V In a preferred embodiment, the bias is towards peptides that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as pseudosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of peptides as well.

Thus, a number of molecules or protein domains are suitable as starting points for the generation of biased randomized peptides. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Generally, at least 4, preferably at least 10, more preferably at least 15 amino acid positions need to be randomized; again, more are preferable if the randomization is less than perfect.

In a preferred embodiment, the random library may have leucines or isoleucines fixed every 7 residues to bias it to a leucine or isoleucine zipper motif.

In a preferred embodiment, the optional C- or N-cap residues, in the case of a helix-biased library, may be fixed and not random would be strong helix formers. For a stronger helical bias, there could be at least 2–3 turns of capping residues, or up to 11–12 amino acids. They could also be (pro)$_n$, to provide a poly-proline helix at the C- or N-terminus. When the C-or N-terminus forms a stable secondary structure such as an alpha helix or a poly-proline helix, it will be resistant to proteolysis, which would be an advantage for the stability of the library within the cell. Explicit N- and C-cap helix stabilizing sequences or residues can be included both at the N-termini and C-termini, respectively [Betz and DeGrado, Biochem. 35:6955–62 (1996); Doig et al. Prot. Sci. 6:147–155 (1997); Doig and Baldwin, Prot. Sci. 4:1325–36 (1995); Richardson and Richardson, Science 240:1648–52 (1988). These sequences are incorporated by reference].

In a preferred embodiment, a library with a more extended structural bias is constructed, wherein weaker helix formers would be fused at each end of the random region, or one or more. glycines would be included in the spacer region and C- or N-cap region.

In another preferred embodiment, a library with a more extended structural bias is constructed by omitting the helix N- or C-cap residues. In this embodiment, the random residues would be selected from all 20 natural L-amino acids.

In another preferred embodiment, a dual library may be constructed with fusion peptides at both the N-and C-terminus of β-lactamase and the resulting library has the following schematic structure: "(+/− optional N-cap residues)-random peptide library-spacer residues-N-terminus-BLA-C-terminus-spacer residues-random peptide library-(+/− optional C-cap residues)". In this case, since the β-lactamase N- and C-terminal helices are adjacent and parallel (i.e. they run in the same direction), such a library could be biased to have two adjacent helices sticking out from the β-lactamase structure in a coiled-coil fashion.

In a preferred embodiment, this bias is accentuated by inclusion of the spacer sequences KLEALEG (Monera et al., supra) or VSSLESK [Graddis et al., Biochem. 32:12664–71 (1993)] between the random peptide library and that of β-lactamase. Alternatively, the spacer sequence VSSLESE could be included between one random peptide library and β-lactamase, and the spacer sequence VSSLKSK could be included between the second random peptide library (e.g., after adjustments of the number of intervening amino acids to keep these in register) and the other terminus of β-lactamase (Graddis et al., supra). These two helix heptad repeats may help bind the two potential helices together.

In a preferred embodiment, the bias of the two adjacent random peptide libraries to a coiled coil is further increased by fixing positions in the sequence such that a number of random residues will be inserted on the surface of the two helices while the fixed residues in the sequence may reside at the interface between the two helices in a parallel coiled coil. For this fusion protein, the two helices composing the random peptide library may be set in register lengthwise by insertion of one or more helix forming residues as appropriate. FIG. 3 shows a helical wheel representation of a parallel coiled coil (see Gradis et al., supra). Positions a, a', d, and d' would be fixed since these are at the core of the coiled coil structure. If these were the only fixed residues and n=5 (see below), the total number of random residues in the library would be 18. The size of the library thus be controlled by n. Residues in positions c, c', f, f', b and b' may be randomized and would present the face of the helix available for binding to targets. Thus, in each coiled coil library, the sequence could be schematically structured as: "BLA-spacer residues-a-b-c-d-e-f-g-(a-b-c-d-e-f-g-)n-C-cap residues and/or N-cap residues-a'-b'-c'-d'-e'-f'-g'-(a'-b'-c'-d'-e'-f -g'-)n-spacer residues-BLA.

In a preferred embodiment, in this scheme the fixed residues a, a', d, and d' are combinations of hydrophobic strong helix forming residues such as ala, val, leu, g and g' are lys, and e and e' are glu (or alternatively lys, when e and e' are glu). Positions e, e', g, and g' may be fixed to further stabilize the coiled coil with salt bridges. Positions b, b', c, c', f and f', may be random residues.

In another preferred embodiment, a library with less helical bias is generated having more random residues on the surface of the helix. In this embodiment, positions g and g' and e and e' may be random residues as well. In the schematically presented libraries of above, n would be 1, 2, 3, 4, 5 or more.

In another preferred embodiment, an alternative set of fixed residues is used to generate a bias to a parallel coiled coil. After the two helices were aligned (i.e. the ends put in register) in the β-lactamase structure, the fixed positions include ala in a and a' leu in d and d', glu in e and e', lys in g and g', and random residues in the remaining positions. In this embodiment, g and g' may also be randomized.

In a preferred embodiment, biased SH-3 domain-binding oligonucleotides/peptides are made. SH-3 domains have been shown to recognize short target motifs (SH-3 domain-binding peptides), about ten to twelve residues in a linear sequence, that can be encoded as short peptides with high affinity for the target SH-3 domain. Consensus sequences for SH-3 domain binding proteins have been proposed. Thus, in a preferred embodiment, oligos/peptides are made with the following biases 1. XXXPPXPXX, (SEQ ID NO:6) Wherein X is a randomized residue.
2. (within the positions of residue positions 11 to −2):

```
                                          (SEQ ID NO:63)
       11  10   9   8   7   6   5   4   3   2
Met Glyaa11aa10 aa9 aa8 aa7 Arg Pro Leu Pro Pro 1   0  -1  -2
hyd Pro hyd hyd Gly Gly Pro Pro STOP
                                          (SEQ ID NO:62)
atg ggc nnk nnk nnk nnk nnk aga cct ctg cct cca sbk ggg sbk sbk gga ggc cca cct TAA1.
```

In this embodiment, the N-terminus flanking region is suggested to have the greatest effects on binding affinity and is therefore entirely randomized. "Hyd" indicates a bias toward a hydrophobic residue, i.e. -Val, Ala, Gly, Leu, Pro, Arg. To encode a hydrophobically biased residue, "sbk" codon biased structure is used. Examination of the codons within the genetic code will ensure this encodes generally hydrophobic residues. s=g,c; b=t, g, c; v=a, g, c; m=a, c; k=t, g; n=a, t, g, c.

In general, the random peptides range from about 4 to about 50 residues in length, with from about 5 to about 30 being preferred, and from about 10 to about 20 being especially preferred.

The random peptide(s) can be fused to a scaffold in a variety of positions, as is more fully outlined herein, to form fusion polypeptides.

In a preferred embodiment, in addition to the scaffold protein and the peptide, the fusion proteins of the present invention preferably include additional components, including, but not limited to, fusion partners, including linkers.

By "fusion partner" herein is meant a sequence that is associated with the random peptide that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the peptides in a conformationally restricted or stable form; b) targeting sequences, defined below, which allow the localization of the peptide into a subcellular or extracellular compartment; c) rescue sequences as defined below, which allow the purification or isolation of either the peptides or the nucleic acids encoding them; d) stability sequences, which confer stability or protection from degradation to the peptide or the nucleic acid encoding it, for example resistance to proteolytic degradation; e) linker sequences, which conformationally decouple the random peptide elements from the scaffold itself, which keep the peptide from interfering with scaffold folding; or f), any combination of a), b), c), d) and e) as well as linker sequences as needed.

In a preferred embodiment, the fusion partner is a presentation structure. By "presentation structure" or grammatical equivalents herein is meant a sequence, which, when fused to peptides, causes the peptides to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmacophore models and pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below, in which elements of the presentation structure are included within the random peptide sequence. To increase the functional isolation of the randomized expression product, the presentation structures are selected or designed to have minimal biologically activity when expressed in the target cell.

Preferred presentation structures maximize accessibility to the peptide by presenting it on an exterior surface such as a loop, and also cause further conformational constraints in a peptide. Accordingly, suitable presentation structures include, but are not limited to, dimerization sequences, minibody structures, loops on β-turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows:    MGC<u>AALESEVSALESEVASLE</u>

SEVAALGRGDMP<u>LAAVKSKL</u>
<u>SAVKSKLASVKSKLAA</u>CGPP (SEQ ID NO:7). The underlined regions represent a coiled-coil leucine zipper region defined previously (see Martin et al., EMBO J. 13(22):5303–5309 (1994), incorporated by reference). The bolded GRGDMP region (SEQ ID NO:8) represents the loop structure and when appropriately replaced with randomized peptides (i.e. peptides, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQATS<u>GFTFSHF</u>YMEWVRGGEYIAASR <u>HKHNKY</u>TTEYSASVKGRYIVSRDTSQSILYLQ KKKGPP (SEQ ID NO:9). The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXl sites on the termini.

In a preferred embodiment, the presentation structure is a sequence that contains generally two cysteine residues, such that a disulfide bond may be formed, resulting in a conformationally constrained sequence. This embodiment is particularly preferred ex vivo, for example when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the presentation sequence confers the ability to bind metal ions to confer secondary structure. Thus, for example, C2H2 zinc finger sequences are used; C2H2 sequences have two cysteines and two histidines placed such that a zinc ion is chelated. Zinc finger domains are known to occur independently in multiple zinc-finger peptides to form structurally independent, flexibly linked domains. See J. Mol. Biol. 228:619 (1992). A general consensus sequence is (5 amino acids)-C-(2 to 3 amino acids)-C-(4 to 12 amino acids)-H-(3 amino acids)-H-(5 amino acids). A preferred example would be -FQCEEC (SEQ ID NO:10)- random peptide of 3 to 20 amino acids-HIRSHTG(SEQ ID NO:11)-.

Similarly, CCHC boxes can be used (see Biochem. Biophys. Res. Commun. 242:385 (1998)), that have a consensus seqeunce -C-(2 amino acids)-C-(4 to 20 random peptide)-H-(4 amino acids)-C- (see Bavoso et al., Biochem. Biophys. Res. Comm. 242(2):.385(1998), hereby incorporated by reference. Preferred examples include (1) -VKCFNC(SEQ ID NO:12)- 4 to 20 random amino acids-HTARNCR(SEQ ID NO:13)-, based on the-nucleocapsid protein P2; (2) a sequence modified from tehat of the naturally occuring zinc-binding peptide of the Lasp-1 LIM domain (Hammarstrom et al., Biochem. 35:12723 (1996)); and (3) -MNPNCARCG(SEQ ID NO:14)- 4 to 20 random amino acids-HKACF(SEQ ID NO:15)-, based on the nmr structural ensemble 1ZFP (Hammarstrom et al., Biochem. 35 U.S.C. 35(39):12723 (1996).

In a preferred embodiment, the presentation structure is a dimerization sequence, including self-binding peptides. A dimerization sequence allows the non-covalent association of two peptide sequences, which can be the same or different, with sufficient affinity to remain associated under normal physiological conditions. These sequences may be used in several ways. In a preferred embodiment, one terminus of the random peptide is joined to a first dimerization sequence and the other terminus is joined to a second dimerization sequence, which can be the same or different from the first sequence. This allows the formation of a loop upon association of the dimerizing sequences. Alternatively, the use of these sequences effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two different sequences that associate. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure. The use of dimerization sequences allows the "circularization" of the random peptides; that is, if a dimerization sequence is used at each terminus of the peptide, the resulting structure can form a "stem-loop" type of structure. Furthermore, the use of dimerizing sequences fused to both the N- and C-terminus of the scaffold such as GFP forms a noncovalently cyclized scaffold random peptide library.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods. See U.S. Ser. No. 60/080,444, filed Apr. 2, 1998, hereby incorporated by reference in its entirety. Particularly preferred dimerization peptide sequences include, but are not limited to, -EEFLIVKKS (SEQ ID NO:16)-, EEFLIVKKS-, (SEQ ID NO:16)-FESIKLV-, (SEQ ID NO:18) VSIKFEL (SEQ ID NO:19)-.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the peptides to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val)(SEQ ID NO:20), Kalderon (1984), et al., Cell, 39:499–509; the human retinoic acid receptor-β nuclear localization signal (ARRRRP (SEQ ID NO:21); NFκB p50 (EEVQRKRQKL (SEQ ID NO:22); Ghosh et al., Cell 62:1019 (1990); NFκB p65 (EEKRKRTYE; (SEQ ID NO:23) Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp) (SEQ ID NO:24), Dingwall, et al., Cell, 30:449458 , 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized epression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8 , ICAM-2, IL-8R, CD4 and LFA-1.

Useful sequences include sequences from: 1) class I integral membrane proteins such as IL-2 receptor β-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor β-chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:25); Nakauchi et al., PNAS USA 82:5126 (1985) and 1–21 in the case of ICAM-2 (MSSFGYRTLTVALFTLICCPG; (SEQ ID NO:26) Staunton et al., Nature (London) 339:61 (1989)). These leader sequences deliver the construct to the membrane while the hydrophobic transmembrane domains, placed 3' of the random peptide region, serve to anchor the construct in the membrane. These transmembrane domains are encompassed by amino acids 145–195 from CD8 (PQRPEDCRPRGSVKGTGLDFACDIYIWAPLAGIC VALLLSLIITLICYHSR; (SEQ ID NO:27) Nakauchi, supra), and 224–256 from ICAM-2 (MVIIVTVVSVLLSLFVTSVLLCFIFGQHLRQQR; (SEQ ID NO:28) taunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:29), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:30) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL, (SEQ ID NO:31) with the bold cysteines being palmitolyated; Stoffel et al., J. Biol. Chem 269:27791 (1994)); from rhodopsin (KQFRNCMLTSLCCGKNPLGD (SEQ ID NO:32); Barnstable et al., J. Mol. Neurosci. 5(3):207 (1994)); and the p21 H-ras 1 protein (LNPPDESGPGCMSCKCVLS (SEQ ID NO:33); Capon et al., Nature 302:33 (1983)).

In a preferred embodiment, the targeting sequence is a lysozomal targeting sequence, including, for example, a lysosomal degradation sequence such as Lamp-2 (KFERQ; (SEQ ID NO:34) Dice, Ann. N.Y. Acad. Sci. 674:58 (1992); or lysosomal membrane sequences from Lamp-1 (MLIPIAGFFALAGLVLIVLIAYLIGRKRSHAGYQTI, (SEQ ID NO:35) Uthayakumar et al., Cell. Mol. Biol. Res. 41:405 (1995)) or Lamp-2 (LVPIAVGAALAGVLILVLLAYFIGLKHHHAGYEQF, (SEQ ID NO:36) Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:37); Schatz, Eur. J. Biochem. 165:1–6 (1987)); mitochondrial inner membrane sequences (yeast cytochrome c oxidase subunit IV; MLSLRQSIRFFKPATRTLCSSRYLL; (SEQ ID NO:38) Schatz, supra); mitochondrial intermembrane space sequences (yeast cytochrome c1; MFSMLSKRWAQRTL-SKSFYSTATGAASKS-GKLTQKLVTAGVAAAGITASTLLYADSLTAEAMTA (SEQ ID NO:39); Schatz, supra) or mitochondrial outer membrane sequences (yeast 70 kD outer membrane protein; MKSFITRNKTAILATVAATG-TAIGAYYYYNQLQQQQQRGKK; (SEQ ID NO:40) Schatz, supra).

The target sequences may also be endoplasmic reticulum sequences, including the sequences from calreticulin (KDEL; (SEQ ID NO:41 ) Pelham, Royal Society London Transactions B; 1–10 (1992)) or adenovirus E3/19K protein (LYLSRRSFIDEKKMP; (SEQ ID NO:42) Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS, (SEQ ID NO:43) with the bold cysteine farnesylated; Capon, supra), geranylgeranylation sequences (for example, protein rab-5A; LTEPTQPTRNQCCSN, (SEQ ID NO:44) with the bold cysteines geranylgeranylated; Farnsworth, PNAS USA 91:11963 (1994)); or destruction sequences (cyclin B1; RTALGDIGN; (SEQ ID NO:45) Klotzbucher et al., EMBO J. 1:3053 (1996)).

In a preferred embodiment, the targeting sequence is a secretory signal sequence capable of effecting the secretion of the peptide. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure, see FIG. 3. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS; (SEQ ID NO:46) Villinger et al. J. Immunol. 155:3946 (1995)), growth hormone (MATGSRTSLLLAFGLLCLPWLQEGS AFPT; (SEQ ID NO:47) Roskam et al., Nucleic Acids Res. 7:30 (1979)); preproinsulin (MALWMRLLPLL ALLAL-WGPDPAAAFVN; (SEQ ID NO:48) Bell et al., Nature284:26 (1980)); and influenza HA protein (MKAKLLVLLYAFVAGDQI; (SEQ ID NO:49) Sekiwawa et al., PNAS 80:3563)), with cleavage between the non-underlined-underlined junction. A particularly preferred secretory signal sequence is the signal leader sequence from the secreted cytokine IL4, which comprises the first 24 amino acids of IL-4 as follows: MGLTSQLLPPLFFLLA-CAGNFVHG (SEQ ID NO:50).

In a preferred embodiment, the fusion partner is a rescue sequence. A rescue sequence is a sequence which may be used to purify or isolate either the peptide or the nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, GST, and Strep tag I and II.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the peptide or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the peptide structure. Thus, preferred stability sequences are as follows: $MG(X)_n GGPP$ (SEQ ID NO:51), where X is any amino acid and n is an integer of at least four. Thus, the terms "N-cap", "N-cap residues", "N-cap sequence" or grammatical equivalents thereof refer to a sequence conferring stability, particularly proteolytic stability, when fused to the N-terminus of a peptide, or to the N-terminus of a scaffold protein, or to the N-terminus of a presentation structure. Similarly, the terms "C-cap", "C-cap residues", "C-cap sequence" or grammatical equivalents thereof refer to a sequence conferring stability, particularly proteolytic stability, when fused to the N-terminus of a peptide, or to the N-terminus of a scaffold protein, or to the N-terminus of a presentation structure.

The fusion partners may be placed anywhere (i.e. N-terminal, C-terminal, internal) in the structure as the biology and activity permits. In addition, while the discussion has been directed to the fusion of fusion partners to the peptide portion of the fusion polypeptide, it is also possible to fuse one or more of these fusion partners to the scaffold portion of the fusion polypeptide. Thus, for example, the scaffold may contain a targeting sequence (either N-terminally, C-terminally, or internally, as described below) at one location, and a rescue sequence in the same place or a different place on the molecule. Thus, any combination of fusion partners and peptides and scaffold proteins may be made.

In a preferred embodiment, the fusion partner includes a linker or tethering sequence. Linker sequences between various targeting sequences (for example, membrane targeting sequences) and the other components of the constructs (such as the randomized peptides) may be desirable to allow the peptides to interact with potential targets unhindered. For example, useful linkers include glycine polymers $(G)_n$, glycine-serine polymers (including, for example, $(GS)_n$, $(GSGGS)_n$ (SEQ ID NO:52) and $(GGGS)_n$, (SEQ ID NO:53) where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted tan residues with longer side chains (see Scheraga, Rev. Computational Chem. 11173–142 (1992)). Secondly, serine is hydrophilic and therefore able to solubilize what could be a globular glycine chain. Third, similar chains have been shown to be effective in joining subunits of recombinant proteins such as single chain antibodies.

In a preferred embodiment, the peptide is connected to the scaffold via linkers. That is, while one embodiment utilizes the direct linkage of the peptide to the scaffold, or of the peptide and any fusion partners to the scaffold, a preferred embodiment utilizes linkers at one or both ends of the peptide. That is, when attached either to the N- or C-terminus, one linker may be used. When the peptide is inserted in an internal position, as is generally outlined below, preferred embodiments utilize at least one linker and preferably two, one at each terminus of the peptide. Linkers are generally preferred in order to conformationally decouple any insertion sequence (i.e. the peptide) from the scaffold structure itself, to minimize local distortions in the scaffold structure that can either destabilize folding intermediates or allow access to GFP's buried tripeptide fluorophore, which decreases (or eliminates GFP's fluorescence due to exposure to exogeneous collisional fluorescence quenchers (see Phillips, Curr. Opin. Structural Biology 7:821 (1997), hereby incorporated by reference in its entireity).

Accordingly, as outlined below, when the peptides are inserted into internal positions in scaffold, preferred embodiments utilize linkers, and preferably $(gly)_n$ linkers, where n is 1 or more, with n being two, three, four, five and six, although linkers of 7–10 or more amino acids are also possible. Generally in this embodiment, no amino acids with β-carbons are used in the linkers.

In another preferred embodiment, the linker comprises the sequence GQGGG (SEQ ID NO:54). Alternatively the linker comprises the sequence GQAGGGG (SEQ ID NO:55). As outlined herein, either linker may be fused to either the N-terminus or C-terminus of a peptide or scaffold protein.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences. As will be appreciated by those in the art, using a base vector that contains a cloning site for receiving random and/or biased libraries, one can cassette in various fusion partners 5' and 3' of the library. In addition, as discussed herein, it is possible to have more than one variable region in a construct, either to together form a new surface or to bring two other molecules together. Similarly, as more fully outlined below, it is possible to have peptides inserted at two or more different loops of the scaffold, preferably but not required to be on the same "face" of scaffold.

The invention further provides fusion nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The candidate nucleic acids are introduced into the cells for screening, as is more fully outlined below. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®), electroporation, viral infection, etc. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

The fusion proteins of the present invention are produced by culturing a host cell transformed with an expression vector containing nucleic acid encoding a fusion protein, under the appropriate conditions to induce or cause expression of the fusion protein. The conditions appropriate for fusion protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C 129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells.

In a preferred embodiment, the fusion proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed Oproximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the fusion nucleic acid.

In a preferred embodiment, the fusion proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the fusion protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the fusion protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, fusion proteins are produced in insect cells. Expression vectors for the transformation of insect cells, and in particular, baculovirus-based expression vectors, are well known in the art.

In a preferred embodiment, fusion protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the fusion polypeptides of the invention may be further fused to other proteins, if desired, for example to increase expression.

In one embodiment, the fusion nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

The fusion nucleic acids are introduced into the cells to screen for peptides capable of altering the phenotype of a cell.

In a preferred embodiment, a first plurality of cells is screened. That is, the cells into which the fusion nucleic acids are introduced are screened for an altered phenotype. Thus, in this embodiment, the effect of the bioactive peptide is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the peptide molecular library, i.e. a different peptide (or nucleic acid encoding the peptide), although as will be appreciated by those in the art, some cells within the library may not contain a peptide, and some may contain more than one species of peptide. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the fusion nucleic acids are introduced into a first plurality of cells, and the effect of the peptide is screened in a second or third plurality of cells, different from the first plurality of cells, i.e. generally a different cell type. That is, the effect of the bioactive peptide is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the peptide (for example, when inducible promoters are used).

Thus, the methods of the present invention comprise introducing a molecular library of fusion nucleic acids encoding randomized peptides fused to scaffold into a plurality of cells, a cellular library. Each of the nucleic acids comprises a different nucleotide sequence encoding scaffold with a random peptide. The plurality of cells is then screened, as is more fully outlined below, for a cell exhibiting an altered phenotype. The altered phenotype is due to the presence of a bioactive peptide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive peptide can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the fusion nucleic acid was introduced; in other embodiments, the altered phenotype is detected in a second cell which is responding to some molecular signal from the first cell.

An altered phenotype of a cell indicates the presence of a bioactive peptide, acting preferably in a transdominant way. By "transdominant" herein is meant that the bioactive peptide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-I, or Herpes viridae family members, or Respiratory Syncytia Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In a preferred embodiment, once a cell with an altered phenotype is detected, the presence of the fusion protein is verified, to ensure that the peptide was expressed and thus that the altered phenotype can be due to the presence of the peptide. As will be appreciated by those in the art, this verification of the presence of the peptide can be done either before, during or after the screening for an altered phenotype. This can be done in a variety of ways, although preferred methods utilize FACS techniques.

Once the presence of the fusion protein is verified, the cell with the altered phenotype is generally isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the fusion nucleic acid and/or the bioactive peptide (i.e. the fusion protein) is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the fusion protein is isolated using a rescue sequence. Thus, for example, rescue sequences comprising epitope tags or purification sequences may be used to pull out the fusion protein using immunoprecipitation or affinity columns. In some instances, as is outlined below, this may also pull out the primary target molecule, if there is a sufficiently strong binding interaction between the bioactive peptide and the target molecule. Alternatively, the peptide may be detected using mass spectroscopy.

Once rescued, the sequence of the bioactive peptide and/or fusion nucleic acid is determined. This information can then be used in a number of ways.

In a preferred embodiment, the bioactive peptide is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive peptide is used to generate more candidate peptides. For example, the sequence of the bioactive peptide may be the basis of a second round of (biased) randomization, to develop bioactive peptides with increased or altered activities. Alternatively, the second round of randomization may change the affinity of the bioactive peptide. Furthermore, it may be desirable to put the identified random region of the bioactive peptide into other presentation structures, or to alter the sequence of the constant region of the presentation structure, to alter the conformation/shape of the bioactive peptide. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive peptide or the bioactive nucleic acid encoding it is used to identify target molecules, i.e. the molecules with which the bioactive peptide interacts. As will be appreciated by those in the art, there may be primary target molecules, to which the bioactive peptide binds or acts upon directly, and there may be secondary target molecules, which are part of the signalling pathway affected by the bioactive peptide; these might be termed "validated targets".

In a preferred embodiment, the bioactive peptide is used to pull out target molecules. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signalling pathways may be elucidated. Similarly, bioactive peptides specific for secondary target molecules may also be discovered, to allow a number of bioactive peptides to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive peptide is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then random libraries introduced into these cells, to select for bioactive peptides which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive peptide will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive peptides capable of blocking the ability of the growth factor or cytokine to stimulate the tumor cell. The introduction of random libraries into specific tumor cells with the addition of the growth factor or cytokine, followed by selection of bioactive peptides which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have random libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the random libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of bioactive peptides which restore the constitutive function of the brca-1 or brca-2 genes, and other tumor suppressor genes important in breast cancer such as the adenomatous polyposis coli gene (APC) and the Drosophila discs-large gene (Dlg), which are components of cell-cell junctions. Mutations of brca-1 are important in hereditary ovarian and breast cancers, and constitute an additional application of the present invention.

In a preferred embodiment, the methods of the present invention are used to create novel cell lines from cancers from patients. A retrovirally delivered short peptide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Ebstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing nucleic acids encoding peptides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive peptides are inserted into cardiomyocytes, the cells are subjected to the insult, and bioactive peptides are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive peptides, followed by the application of arrythmogenic insults, with screening for bioactive peptides that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive peptides which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive peptides are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive peptides which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for peptides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive peptides can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive peptide libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive peptide libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive peptides can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive peptides that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive peptides that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive peptides isolated which decrease the rate of growth of these cells.

In a preferred embodiment, the present methods are useful in the regulation or inhibition of keloid formation (i.e. excessive scarring). Candidate libraries inserted into skin connective tissue cells isolated from individuals with this condition, and bioactive peptides isolated that decrease proliferation, collagen formation, or proline incorporation. Results from this work can be extended to treat the excessive scarring that also occurs in bum patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate libraries can be inserted into skin connective tissue cells, and bioactive peptides isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive peptides can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive peptides isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a random, cyclized peptide library of the general sequence CNNNNNNNNNNC (SEQ ID NO:56) or C-(X)$_n$-C. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus usesCD44) and to fuse with cells (HIV uses chemokine receptor). Candidate libraries can be inserted into target cells known to be permissive to these viruses, and bioactive peptides isolated which block the ability of these viruses to bind and fuse with specific target cells.

In a preferred embodiment, the present invention finds use with infectious organisms. Intracellular organisms such as mycobacteria, listeria, salmonella, pneumocystis, yersinia, leishmania, *T. cruzi*, can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive peptides selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive peptides can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive peptides can be isolated that confer protection, when these cells are treated with these specific antibiotics.

Furthermore, the present invention finds use in screening for bioactive peptides that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactive peptides can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive peptides can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate libraries can be introduced into tumor cell lines (primary and cultured) that have demonstrated specific or multiple drug resistance. Bioactive peptides can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactive peptides selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1-17, may be selected, or agents that bind cytokines such as TNF-α, before they bind their receptor.

Antigen processing by mononuclear leukocytes (ML) is an important early step in the immune system's ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive peptides selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive peptides which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive peptide sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e. within a signalling pathway, to localize the effects to a functional area of interest.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entireity.

EXAMPLES

Example 1

Selection of Loop Insertion Sites

One example concerns the insertion of sequences of the compostion linker-test sequence-linker into defined sites within engineered GFP loops most likely to tolerate insertions. These loops were selected based on having mobility in the loop or tip of the loop well above that of the most rigid parts of the beta-can structure (Yang et al., Nature Biotechnology 14, 1246–9, 1996; Ormo et al., Science 273, 1392–5, 1996). The loops of most interest are those which are not rigidly coupled to the beta-can structure of the rest of GFP; this lack of rigid coupling may allow the most tolerance for sequence additions within the loops in a library construct. Loops can be selected as those which have the highest temperature factors in the crystal structures, and include loops 130–135, 154–159, 172–175, 188–193, and 208–216 in a GFP monomer. The temperature factor of the loop can be artificially increased by including flexible amino acids such as glycine in the linkers (see below).

The most promising insert sites were selected by removing residues at the termini of the loops whose side chains extended into solution and did not contact either the GFP β-can or other parts of the loops. Loop residues whose side chains bound to other parts of GFP were left unreplaced so as to minimize the likelihood of strong conformational coupling between the random sequences and GFP, which could lead to misfolded protein and/or could diminish the number of fluorescent GFP-fused random peptides by distorting the base of the loop and allowing collisional quenchers access to the fluorophore.

| loop | insert location |
|---|---|
| 1 | replace asp 133 with insert; can't remove glu 132 as carboxylate binds to other residue side chains; this is a very short loop |
| 2 | replace gln 157 and lys 156 with entire insert; lys 156 and gln 157 side chains protrude into solution; lys 158 ion pairs with asp 155 to help close loop so these are generally retained; avoid removing asn 159 as it contacts the main protein body in a number of spots |
| 3 | replace asp 173 with insert, as it is at the outer end of the loop; avoid replacing glu 172 as side chain contacts other side chains in the folded structure; could replace gly 174 too |
| 4 | replace residues 189–192 (gly-asp-gly-pro) with insert; this is not so much a loop as a strand connecting two separated chains; P192, G191, D190 and G189 all protrude into solution and don't appear to form tight contacts with the main protein body; so they appear replaceable |
| 5 | replace asn 212, glu 213 and lys 214 with insert; lys 214 side chain protrudes out into solution; glu 213 helps form the turn as it's side chain binds other side chains in the loop, thus its replacement may cause problems in maintaining a native loop conformation; asn 212 side chain protrudes into solution |

Example 2

Selection of a Test Insert Sequence

To allow a maximal number of different loop inserts or replacements in GFP to fold properly into a fluorescent GFP construct, it may be important to carefully select the linker sequences between the native GFP structure and the inserted sequences making up the actual library inserted into the loop. One way to prevent problems in GFP folding is to conformationally decouple any insert sequence from the GFP structure itself, to minimize local distortions in GFP structure which could either destabilize folding intermediates or could allow access to GFP's buried tripeptide fluorophore of exogenous collisional fluorescence quenchers (Phillips, supra). This can be done by inserting multiple highly flexible amino acid residues between GFP and the library, which impose minimal conformational constraints on the GFP. One or more glycines are ideal for this purpose, as glycine accesses significantly more phi-psi space than even alanine, and is much less restricted than residues with longer side chains (Scheraga, H.A., (1992), "Predicting three-dimensional structures of oligopeptides", in Reviews in Computational Chemstry III, p. 73–142). Thus to optimize the chances of the loop inserts not affecting GFP structure, -(gly)$_n$- is inserted between these two sequences at each loop containing a library. Minimally n=1, but more optimally n≧2.

The initial two test inserts were: 1: -GGGGYPYDVPDYASLGGGG- and 2: -GGGG-YPYD-GGGG (SEQ ID NO: 58). The first sequence was an 19mer insert (approximately the intended library size) with the influenza hemagglutinin (HA) epitope tag embedded, with glycines added to each end to match the epitope inserted into the dimerizer-folded scaffold, and to add flexibility to the epitope to allow a conformation which binds to polyclonal antisera. This allowed estimation by Western blotting of the expression level of the different constructs. The second insert is truncated to examine the effect on GFP fluorescence of a shorter peptide.

Example 3

Mean Fluorescence of GFP with Test Inserts 1 and 2 in Loops 1–5, Expressed in E. coli The GFP used is EGFP (Clontech Inc., Palo Alto, Calif.) and the two test sequences were inserted at the sites indicated in example 1. An equal number of bacteria (20000) representing clones of a single colonies were analyzed by fluorescence-activated cell sorting on a MoFlo cell sorter (Cytomation Inc., Ft. Collins, Colo.). Intensity of FL1 was averaged. The relative fluorescence intensity was calculated as (WT fluorescence−fluorescence of loop insert)/(WT fluorescence−bkd)×100%. Constructs with insert 1 in loops 1 and 5 were not expressed due to cloning difficulties. Equal amounts of cell lysate from each loop insert were run on a 10% SDS gel and blotted to PVDF. GFP was detected with anti-GFP antibody and the bands were observed using chemiluminescent detection. The intensity of individual bands was measured using a Sharp JX-330 scanning densitomer and BioImage software. The specific fluorescence was calculated as the ratio of the relative fluorescence to the relative intensity of the Western blot band.

TABLE 1

Mean fluorescence of GFP with different insertion sequences in loops 1–5.

| loop | relative fluorescence | | relative intensity: Western | | specific fluorescence | |
|---|---|---|---|---|---|---|
| | insert 2 12 mer | insert 1 19 mer | insert 2 | insert 1 | insert 2 | insert 1 |
| wild type (no insert) | 1.00 | 1.00 | 1.00 | 1.00 | 1.00 | 1.00 |
| background | 0 | 0 | | | | |
| 1 | 0 | — | 0.179 | — | 0 | — |
| 2 | 0.198 | 0.10 | 0.165 | 0.189 | 1.20 | 0.53 |
| 3 | 0.612 | 0.399 | 0.467 | 0.68 | 1.3 | 0.59 |
| 4 | 0.119 | 0.034 | 0.135 | 0.0196 | 0.88 | 1.73 |
| 5 | 0 | — | 0.159 | — | 0 | — | insert 1: -GGGG-YPYDVPDYASL-GGGG- (SEQ ID NO: 57) 2: -GGGG-YPYD-GGGG- (SEQ ID NO: 58)

The results in Table 1 show that in E. coli, the defined loop 2, 3 and 4 insertion sites support GFP folding and fluorescence for both the 12mer and 19mer inserts, while inserts in sites 1 and 5 allow expression of GFP without fluorescence for the 12mer insert. Libraries in these sites 20 may thus be useful for screening using other methods for selecting positives than GFP fluorescence. For insertion sites 2, 3 and 4 the fluorescence for a 12mer insert with multiple glycines at each end is at least 10% of that of wild type GFP. The highest fluorescence for the 12mer insert was obtained with insertion in the loop 3 site, while the lowest was obtained from loop 4. This appeared to be due to differing expression levels for each construct. For the larger 19mer insert, the highest fluorescence was again obtained with insertion in the loop 3 site, while the lowest was obtained from insertion into the loop 2 site, again due to higher apparent expression levels for the loop 3 insert GFP. Again, the highest specific fluorescence was obtained with loop 4. This suggests that libraries inserted into loop 4, combined with strong promoters to enhance expressed levels of the GFP-library members, will allow screening of these libraries as well as loop 2 and 3 libraries. For the 19mer insert sequence, the loop 2, 3 and 4 inserts all give fluorescence of at least 1% of wild type, and thus should allow screening of libraries in all three loops.

The Western blot results suggest that shorter inserts in loops 1 and 5 allow GFP expression at levels as high or higher than those of loops 2 and 4, albeit without fluorescence. Thus random peptide libraries inserted into these loops can be used to screen cells for phenotypic changes, but the screen for the presence of the library member will have to rely on some property other than GFP fluorescence, such as a readout reflecting a phenotypic change in the cell itself.

Example 4

Mean Fluorescence of GFP with Test Inserts 1 and 2 in Loops 2–4, When Expressed in Jurkat E Cells Insert sequences identical to those shown in example 3 above were used with GFP when expressed in Jurkat E cells. GFP was expressed using the LTR of the retroviral expression vector, and the Jurkats were infected using Phoenix 293 helper cells. After 48 hours of infection, the Jurkats were subjected to FACS analysis using a Becton-Dickinson FAC-SCAN cell sorter. For each insert $10^4$ cells were gated using forward- vs. side-scatter selection to isolate live cells. Live cells were selected in a second round using propidium iodide fluorescence, and were then sorted in FL1 on the intensity of their GFP fluorescence. The infection levels of the Jurkat cells with the different constructs were in the range of 30.1%–44.9%, giving on average one peptide construct inserted per cell.

TABLE 2

Geometric mean fluorescence of GFP with different insertion sequences in loops 2–4: Jurkat cells.

| | relative fluorescence | |
|---|---|---|
| loop | insert 2 12 mer | insert 1 19 mer |
| wild type (no insert) | 1.00 | 1.00 |
| background | 0.000625 | 0.000625 |
| 2 | 0.324 | 0.088 |
| 3 | 1.01 | 0.254 |
| 4 | 0.188 | 0.0625 | insert 1: -GGGG-YPYDVPDYASL-GGGG-A (SEQ ID NO: 57)
insert 2: -GGGG-YPYD-GGGG- (SEQ ID NO: 58)

These results show that the designed insertion sites in loops 2–4 retain a high level of GFP fluorescence when the inserts are flanked by multiple glycines in the tetrapeptide linkers. Thus an insert of 19 residues appears to retain high levels of fluorescence, suggesting that all three loops will allow insertion of random peptide libraries and their screening. Such screening should require only a level of fluorescence distinguishable from background, or one decade up in FL1.

The successful observation of fluorescence of nearly 10% or more of wild type in GFP with both sequences in the loop 2 insertion site was not seen by Abedi et al. (1998) and suggests that inclusion of the glycine linkers on either side of the insert sequence, combined with excision of residues at the tip of the loop, may make this loop a unique and useful site for insertion of random library sequences. The high levels of relative fluorescence for inserts 1 and 2 in loops 2–4 suggest that the tetraglycine linkers will allow successful insertion of random peptide libraries into these particular sites; shorter libraries may be preferred.

Example 5

Mean Fluorescence of GFP with Test Inserts 1 and 2 in Loops 2–4, When Expressed in Phoenix 293 Cells Insert sequences identical to those shown in example 3 above were used with GFP when expressed in Phoenix 293 cells. GFP was expressed using the 96.7 CMV-promoter driven CRU-5 retroviral expression vector in transfected Phoenix 293 cells. The transfection efficiency was 40–45%. After 48 hours of transfection, the Phoenix 293 cells were subjected to FACS analysis using a Becton-Dickinson FAC-SCAN cell sorter. For each insert approximately $10^4$ cells were gated using forward- vs. side-scatter selection to isolate live cells. Live cells were selected in a second round using propidium iodide fluorescence, and were then sorted in FL1 on the intensity of their GFP fluorescence. The transfection efficiency for all constructs reported was in the range of 24–42%, giving on average one plasmid/cell expressing the GFP construct.

TABLE 3

Geometric mean fluorescence of GFP with different insertion sequences in loops 2–4: Phoenix 293 cells.

| loop | relative fluorescence | | relative intensity: Western | | specific fluorescence | |
|---|---|---|---|---|---|---|
| | insert 2 12 mer | insert 1 19 mer | insert 2 | insert 1 | insert 2 | insert 1 |
| wild type (no insert) | 1.00 ± .078 | 1.00 ± .078 | 1.00 | 1.00 | 1.00 | 1.00 |
| background | 0.00 | 0.00 | 0 | 0 | | |
| 2 | 1.07 ± .18* | 0.676 ± .078 | 0.44 | 0.40 | 2.43 | 1.69 |
| 3 | 1.32 ± .12* | 0.471 ± .055 | 0.69 | 0.99 | 1.91 | 0.48 |
| 4 | 0.51 ± .08 | 0.422 ± .071 | 0.36 | 0.19 | 1.42 | 2.22 | insert 1: -GGGG-YPYDVPDYASL-GGGG- (SEQ ID NO: 57)  2: -GGGG-YPYD-GGGG- (SEQ ID NO: 58)

The numbers for the relative fluorescence of the loop 2, 3, and 4 inserts are derived from the average value ±1 standard deviation for 1–2 independent clones with the specified insert. The specific fluorescence is the ratio of the relative fluorescence to the Western blot relative intensity. The standard deviation of the relative fluorescence was calculated as [fluorescence of insert/fluorescence of WT {(std. dev of insert fluorescence/insert fluorescence)$^2$+(std. dev. of WT fluorescence/WT fluorescence)$^2$}]$^{0.5}$ (Bevington, P. 1969. Data reduction and error analysis for the physical sciences. New York: McGraw Hill, p. 61–2). Data with an asterisk* was derived from cells with a 60–70% transfection efficiency and so can only be qualitatively compared with the rest of the data.

These results for 293 cells show that in these cells the designed insertion sites in loops 2–4 retain a very high level of GFP fluorescence when the inserts are flanked by multiple glycines in the tetrapeptide linkers, in some cases higher than wild type GFP fluorescence. Thus both inserts of 19 and 12 residues retain high levels of fluorescence, suggesting that all three loops will allow insertion of random peptide libraries and their screening, and that libraries in all three loops are roughly equivalent. The high level of relative fluorescence of loop 3 appears to be mainly due to a higher expression level than the GFP construct with inserts in loops 1 and 2, although the expression levels of all 3 loop-inserts are at least 19% of the wild type GFP levels. Since the specific fluorescence of both inserts in loops 2 and 4 is greater than the insert in loop 3, a higher level of expression could compensate for the overall lower level of fluorescence of these loop 2 and 4 inserts. Since expression of these constructs is with a stronger promoter than expression in *E. coli* or Jurkat cells, this also suggests that use of stronger promoters than the retroviral LTR or promoter in *E coli* will make more loop insertion sites usable for screens.

We claim:

1. A method of screening for bioactive peptides conferring a particular phenotype comprising:
   a) providing cells containing a fusion nucleic acid comprising:
      i) a first nucleic acid encoding a Renilla GFP scaffold protein;
      ii) a second nucleic acid encoding a different random peptide fused to the N-terminus of said scaffold protein; and
      iii) a third nucleic acid encoding a flexible linker between said scaffold and said random peptide; and
   b) screening said cells for an altered phenotype.

2. A method of screening for bioactive peptides conferring a particular phenotype comprising:
   a) providing cells containing a fusion nucleic acid comprising:
      i) a first nucleic acid encoding a Renilla GFP scaffold protein;
      ii) a second nucleic acid encoding a different random peptide fused to the C-terminus of said scaffold protein; and
      iii) a third nucleic acid encoding a flexible linker between said scaffold and said random peptide; and
   b) screening said cells for an altered phenotype.

3. A method of screening for bioactive peptides conferring a particular phenotype comprising:
   a) providing cells containing a fusion nucleic acid comprising:
      i) a first nucleic acid encoding a Renilla GFP scaffold protein;
      ii) a second nucleic acid encoding a different random peptide wherein said second nucleic acid is inserted into said first nucleic acid; and
      iii) a third nucleic acid encoding a first flexible linker between said scaffold and said random peptide; and
   b) screening said cells for an altered phenotype.

4. A method according to claim 3 further comprising a second flexible linker between the other end of said random peptide and said scaffold protein.

5. A method according to claim 1, 2 or 3, wherein said linker replaces at least one amino acid of said scaffold protein.

6. A method according to claim 1, 2 or 3, wherein said linker comprises -(gly)n-, wherein $n \geq 2$.

7. A method according to claim 1, 2 or 3, wherein said Renilla GFP is wild-type.

8. A method according to claim 1, 2 or 3, wherein said Renilla GFP is a variant GFP.

9. A method according to claim 1, 2 or 3 wherein said cells are mammalian cells.

10. A method according to claim 1, 2 or 3 wherein said providing is accomplished by transfecting said cells with a retroviral vector comprising said fusion nucleic acid.

11. The method according to claim 1, 2 or 3, wherein said linker comprises $(GS)_n$, wherein $n \geq 3$.

12. The method according to claim 1, 2 or 3, wherein said linker comprises $(GSGGS)_n$, wherein $n \geq 1$.

13. The method according to claim 1, 2 or 3, wherein said linker comprises $(GGGS)_n$, wherein $n \geq 1$.

14. The method according to claim 1, 2 or 3, wherein said linker comprises GQGGG.

15. The method according to claim 1, 2 or 3, wherein said linker comprises GQAGGGG.

16. The method according to claim 1, 2, or 3, wherein said phenotype is modulation of an immune response.

17. The method according to claim 1, 2, or 3 wherein said cells comprise T-cells and said phenotype is a T-cell response.

18. The method of claim 17, wherein said T-cell response is proliferation in response to antigen presentation.

19. The method according to claim 1, 2, or 3, wherein said cells comprise B cells and said phenotype is a interaction with a specific immunoglobulin.

20. The method according to claim 1, 2, or 3 wherein said phenotype is cytokine production.

21. The method according to claim 20, wherein said cells are macrophages.

22. The method according to claim 20, wherein said cells are monocytes.

23. The method according to claim 1, 2, or 3 wherein said cells are mononuclear leukocytes and said phenotype is antigen processing.

24. The method according to claim 1, 2, or 3 wherein said phenotype is release of inflammatory mediators.

25. The method of claim 24 wherein said cells comprise mononuclear leukocytes.

26. The method of claim 24 wherein said cells comprise mast cells.

27. The method of claim 24 wherein said cells comprise eosinophils.

28. A method of screening for bioactive peptides conferring a particular phenotype comprising:
   a) providing cells containing a fusion nucleic acid comprising:
      i) a first nucleic acid encoding a Renilla GFP scaffold protein;
      ii) a second nucleic acid encoding a different random peptide fused to the N-terminus of said scaffold protein; and iii) a third nucleic acid encoding a linker between said scaffold and said random peptide, wherein said linker comprises -(gly)n-, wherein n≧2; and b) screening said cells for an altered phenotype.

29. A method of screening for bioactive peptides conferring a particular phenotype comprising:

a) providing cells containing a fusion nucleic acid comprising:
i) a first nucleic acid encoding a Renilla GFP scaffold protein;
ii) a second nucleic acid encoding a different random peptide fused to the C-terminus of said scaffold protein; and
iii) a third nucleic acid encoding a linker between said scaffold and said random peptide, wherein said linker comprises -(gly)n-, wherein n≧2; and b) screening said cells for an altered phenotype.

30. A method of screening for bioactive peptides conferring a particular phenotype comprising:

a) providing cells containing a fusion nucleic acid comprising:
i) a first nucleic acid encoding a Renilla GFP scaffold protein;
ii) a second nucleic acid encoding a different random peptide wherein said second nucleic acid is inserted into said first nucleic acid; and
iii) a third nucleic acid encoding a linker between said scaffold and said random peptide, wherein said linker comprises -(gly)n-, wherein n≧2; and b) screening said cells for an altered phenotype.

31. A method of screening for bioactive peptides conferring a particular phenotype comprising:

a) providing cells containing a fusion nucleic acid comprising:
i) a first nucleic acid encoding a Renilla GFP scaffold protein;
ii) a second nucleic acid encoding a different random peptide fused to the N-terminus of said scaffold protein; and
iii) a third nucleic acid encoding a linker between said scaffold and said random peptide, wherein said linker replaces at least one amino acid of said scaffold protein; and b) screening said cells for an altered phenotype.

32. A method of screening for bioactive peptides conferring a particular phenotype comprising:

a) providing cells containing a fusion nucleic acid comprising:
i) a first nucleic acid encoding a Renilla GFP scaffold protein;
ii) a second nucleic acid encoding a different random peptide fused to the C-terminus of said scaffold protein; and
iii) a third nucleic acid encoding a linker between said scaffold and said random peptide, wherein said linker replaces at least one amino acid of said scaffold protein; and b) screening said cells for an altered phenotype.

33. A method of screening for bioactive peptides conferring a particular phenotype comprising:

a) providing cells containing a fusion nucleic acid comprising:
i) a first nucleic acid encoding a Renilla GFP scaffold protein;
ii) a second nucleic acid encoding a different random peptide wherein said second nucleic acid is inserted into said first nucleic acid; and
iii) a third nucleic acid encoding a linker between said scaffold and said random peptide, wherein said linker replaces at least one amino acid of said scaffold protein; and b) screening said cells for an altered phenotype.

* * * * *